US009624195B2

(12) United States Patent
Hu et al.

(10) Patent No.: US 9,624,195 B2
(45) Date of Patent: Apr. 18, 2017

(54) ISOQUINOLINE COMPOUNDS

(71) Applicant: Gilead Sciences, Inc., Foster City, CA (US)

(72) Inventors: Yunfeng Eric Hu, San Mateo, CA (US); Petr Jansa, San Mateo, CA (US); Eric Lansdon, Belmont, CA (US); Richard L. Mackman, Millbrae, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 14/998,131

(22) Filed: Dec. 23, 2015

(65) Prior Publication Data

US 2016/0237062 A1   Aug. 18, 2016

Related U.S. Application Data

(60) Provisional application No. 62/096,769, filed on Dec. 24, 2014.

(51) Int. Cl.
| C07D 401/12 | (2006.01) |
| C07D 217/22 | (2006.01) |
| A61K 31/472 | (2006.01) |
| A61K 31/4725 | (2006.01) |
| A61K 31/497 | (2006.01) |
| A61K 31/501 | (2006.01) |
| A61K 31/506 | (2006.01) |
| A61K 45/06 | (2006.01) |

(52) U.S. Cl.
CPC .......... *C07D 401/12* (2013.01); *A61K 31/472* (2013.01); *A61K 31/4725* (2013.01); *A61K 31/497* (2013.01); *A61K 31/501* (2013.01); *A61K 31/506* (2013.01); *A61K 45/06* (2013.01); *C07D 217/22* (2013.01)

(58) Field of Classification Search
CPC .............. A61K 31/472; A61K 31/4725; A61K 31/497; A61K 31/501; A61K 31/506; A61K 45/06; C07D 217/22; C07D 401/12
See application file for complete search history.

(56) References Cited

U.S. PATENT DOCUMENTS

| 4,675,047 A | 6/1987 | Serban et al. |
| 7,932,262 B2 | 4/2011 | Ramurthy et al. |
| 2002/0055516 A1 | 5/2002 | Miyazaki et al. |
| 2007/0298104 A1* | 12/2007 | Arend ................. C07D 217/26 424/468 |
| 2010/0143301 A1 | 6/2010 | Desai et al. |
| 2011/0039845 A1 | 2/2011 | Kashima et al. |
| 2013/0165489 A1 | 6/2013 | Cocklin et al. |
| 2014/0221356 A1 | 8/2014 | Jin et al. |
| 2014/0221378 A1 | 8/2014 | Miyazaki et al. |
| 2014/0221380 A1 | 8/2014 | Miyazaki et al. |
| 2014/0378443 A1 | 12/2014 | Jorgensen et al. |
| 2016/0237062 A1 | 8/2016 | Hu et al. |
| 2016/0250215 A1 | 9/2016 | Baszczynski et al. |
| 2016/0251347 A1 | 9/2016 | Jansa et al. |

FOREIGN PATENT DOCUMENTS

| WO | WO-01/21598 A1 | 3/2001 |
| WO | WO-01/38315 A1 | 5/2001 |
| WO | WO-01/55140 A1 | 8/2001 |
| WO | WO-02/10136 A1 | 2/2002 |
| WO | WO-02/24667 A1 | 3/2002 |
| WO | WO-2004/030672 A1 | 4/2004 |
| WO | WO-2004/09628 A2 | 11/2004 |
| WO | WO-2004/108711 A1 | 12/2004 |
| WO | WO-2005/035503 A1 | 4/2005 |
| WO | WO-2006/015261 A2 | 2/2006 |
| WO | WO-2006/039718 A2 | 4/2006 |
| WO | WO-2006/045828 A1 | 5/2006 |
| WO | WO-2006/071095 A1 | 7/2006 |
| WO | WO-2006/099301 A2 | 9/2006 |
| WO | WO-2006/110157 A2 | 10/2006 |
| WO | WO-2006/118256 A1 | 11/2006 |
| WO | WO-2007/000240 A1 | 1/2007 |
| WO | WO-2007/012421 A1 | 2/2007 |
| WO | WO-2007/076092 A2 | 7/2007 |
| WO | WO-2007/125405 A2 | 11/2007 |
| WO | WO-2008/011109 A2 | 1/2008 |
| WO | WO-2008/011109 A3 | 1/2008 |
| WO | WO-2008/030455 A2 | 3/2008 |
| WO | WO-2008/030455 A3 | 3/2008 |
| WO | WO-2008/050808 A1 | 5/2008 |
| WO | WO-2008/077550 A1 | 7/2008 |
| WO | WO-2008/077551 A1 | 7/2008 |
| WO | WO-2008/077553 A1 | 7/2008 |
| WO | WO-2008/086462 A2 | 7/2008 |
| WO | WO-2008/122614 A1 | 10/2008 |
| WO | WO-2008/157500 A1 | 12/2008 |

(Continued)

OTHER PUBLICATIONS

Berge, S.M., et al., (1977), "Pharmaceutical Salts" J. Pharma Sci., 66(1):1-19.
Das, K., et al., (2008), "High-resolution structures of HIV-1 reverse transcriptase/TMC278 complexes: Strategic flexibility explains potency against resistance mutations", PROC. NAT. ACAD. SCI., 105(5):1466-1471.
S. Eigler and A. Hirsch, "Chemistry with Graphene and Graphene Oxide—Challenges for Synthetic Chemists" ANGEW. CHEM. INT. ED., (2014), vol. 53, pp. 2-21.
Foster, "Deuterium Isotope Effects in Studies of Drug Metabolism", Trends Pharmacol. Sci., (1984), vol. 5, No. 12, pp. 524-527.

(Continued)

*Primary Examiner* — Sarah Pihonak
(74) *Attorney, Agent, or Firm* — Fish & Richardson P.C.

(57) ABSTRACT

Described herein are compounds of Formula (I) and tautomers and pharmaceutical salts thereof, compositions and formulations containing such compounds, and methods of using and making such compounds.

21 Claims, No Drawings

(56) References Cited

FOREIGN PATENT DOCUMENTS

| | | | |
|---|---|---|---|
| WO | WO-2009/062285 A1 | 5/2009 |
| WO | WO-2009/155121 A2 | 12/2009 |
| WO | WO-2009/155121 A3 | 12/2009 |
| WO | WO-2010/076238 A1 | 7/2010 |
| WO | WO-2010/007374 A1 | 10/2010 |
| WO | WO-2010/18155 A1 | 10/2010 |
| WO | WO-2010/130034 A1 | 11/2010 |
| WO | WO-2011/035416 A1 | 3/2011 |
| WO | WO-2011/161159 A1 | 12/2011 |
| WO | WO-2011/163610 A2 | 12/2011 |
| WO | WO-2011/163610 A3 | 12/2011 |
| WO | WO-2011/156610 A2 | 1/2012 |
| WO | WO-2011/156610 A3 | 1/2012 |
| WO | WO-2012/003497 A1 | 1/2012 |
| WO | WO-2012/003498 A1 | 1/2012 |
| WO | WO-2012/050347 A1 | 4/2012 |
| WO | WO-2012/044090 A2 | 6/2012 |
| WO | WO-2012/044090 A3 | 6/2012 |
| WO | WO-2012/080284 A2 | 6/2012 |
| WO | WO-2012/116237 A2 | 8/2012 |
| WO | WO-2012/116237 A3 | 8/2012 |
| WO | WO-2012/145728 A1 | 10/2012 |
| WO | WO-2013/006738 A1 | 1/2013 |
| WO | WO-2013/006792 A1 | 1/2013 |
| WO | WO-2013/091096 A1 | 6/2013 |
| WO | WO-2013/159064 A1 | 10/2013 |
| WO | WO-2014/100323 A1 | 6/2014 |
| WO | WO-2014/128206 A1 | 8/2014 |
| WO | WO-2014/128213 A1 | 8/2014 |
| WO | WO-2016/105532 A1 | 6/2016 |
| WO | WO-2016/105534 A1 | 6/2016 |
| WO | WO-2016/105564 A1 | 10/2016 |

OTHER PUBLICATIONS

Janssen, P.A., et al., (2005), "In Search of a Novel Anti-HIV Drug: Multidisciplinary Coordination in the Discovery of 4-[[4-[[4-[(1E)-2-Cyanoethenyl]-2,6-dimethylphenyl]amino]-2 pyrimidinyl]amino]benzonitrile (R278474, Rilpivirine)", J. Med. Chem, 48(6):1901-1909.

Johnson, B., et al., (Dec. 5, 2012) "A Comparison of the ability of rilpivirine (TMC278) and selected analogues to inhibit clinically relevant HIV-1 reverse transcriptase mutants", Retrovirology, Biomed Central LTD., London GB, 9(1):99.

Kuroda et al., (2013) "Snapshot of the equilibrium dynamics of a drug bound to HIV-1 reverse transcriptase", Nature Chemistry, pp. 1-8.

Remington, "The Science and Practice of Pharmacy", R. Hendrickson, ed., 21st edition, Lippincott, Williams & Wilkins, Philadelphia, PA, (2005), at p. 732, Table 38-5.

Smith, M.B., et al., (2007), March's Advanced Organic Chemistry, "Reactions, Mechanisms, and Structure", Wiley-Interscience, sixth edition, pp. 1218-1223.

Non Final Office Action mailed Aug. 5, 2016, for U.S. Appl. No. 14/998,042, filed Dec. 23, 2015, eight pages.

Non Final Office Action mailed Oct. 20, 2016, for U.S. Appl. No. 14/998,074, filed Dec. 23, 2015, five pages.

Written Opinion of the International Searching Authority mailed on Mar. 17, 2016, for PCT Application No. PCT/US2015/000460, filed on Dec. 23, 2015, nine pages.

Written Opinion of the International Searching Authority mailed on Mar. 31, 2016, for PCT Application No. PCT/US2015/000310, filed on Dec. 23, 2015, eleven pages.

Written Opinion of the International Searching Authority mailed on Mar. 31, 2016, for PCT Application No. PCT/US2015/000308, filed on Dec. 23, 2015, fourteen pages.

\* cited by examiner

ISOQUINOLINE COMPOUNDS

CROSS-REFERENCE TO RELATED APPLICATIONS

This application claims priority benefit to U.S. Application Ser. No. 62/096,769, filed Dec. 24, 2014, the disclosure of which is herein incorporated by reference in its entirety.

BACKGROUND

While progress has been made in treating HIV and AIDS, HIV infection remains a global health concern. As part of such treatments, non-nucleoside reverse transcriptase inhibitors (NNRTIs) have often been employed, particularly as part of highly active antiretroviral therapy (HAART) treatment regimens. Though potent, drawbacks exist for many of the known NNRTIs as their use has been associated with mutations in the HIV virus that may result in drug resistance. As such, there remains a need for further development of potent NNTRIs.

Described herein are compounds of Formula (I) and pharmaceutically acceptable salts thereof, compositions and formulations containing such compounds, or pharmaceutically acceptable salts thereof, and methods of using and making such compounds, or pharmaceutically acceptable salts thereof.

SUMMARY

In certain embodiments, the present disclosure relates to compounds of Formula (I) or a tautomer thereof,

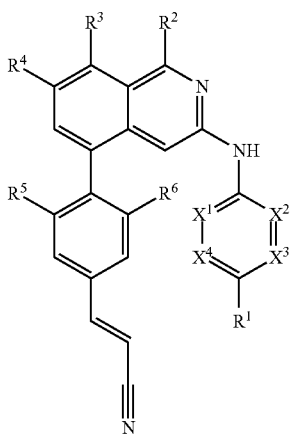

(I)

or pharmaceutically acceptable salt thereof, wherein $X^1$, $X^2$, $X^3$, and $X^4$ are each independently $C(R^7)$ or N, wherein 0 to 2 of $X^1$, $X^2$, $X^3$, and $X^4$ are N;

$R^1$ is —H, —CN, —$OR^a$, $C_{1-6}$ haloalkyl or halogen;

$R^2$ is —H, —$NR^bR^c$, —$SR^a$, —$OR^a$ or $C_{1-6}$ alkyl, wherein $C_{1-6}$ alkyl is optionally substituted with 1, 2, 3, 4 or 5 $R^8$ groups, which may be the same or different;

$R^3$ and $R^4$ are each independently —H, —$OR^a$, halogen, —$NR^bR^c$, —$C(O)OR^a$, —CN, —$C(O)NR^bR^c$, —NHC(O)$NR^bR^c$, —OC(O)$NR^bR^c$, $CH_2C(O)NR^bR^c$, $C_{1-6}$ alkyl or $C_{1-6}$ heteroalkyl, wherein each $C_{1-6}$ alkyl or $C_{1-6}$ heteroalkyl is optionally substituted with 1, 2, 3, 4 or 5 $R^8$ groups, which may be the same or different;

$R^5$ and $R^6$ are each independently halogen, —$OR^a$ or $C_{1-6}$ alkyl, wherein each $C_{1-6}$ alkyl is optionally substituted with 1, 2, 3, 4 or 5 $R^8$ groups, which may be the same or different;
each $R^7$ is independently —H, halogen, —$OR^a$ or $C_{1-6}$ alkyl, wherein each $C_{1-6}$ alkyl is optionally substituted with 1, 2, 3, 4 or 5 $R^8$ groups, which may be the same or different;
each $R^8$ is independently $C_{1-6}$ alkyl, $C_{1-6}$ heteroalkyl, aryl, heteroaryl, halogen, —$OR^a$, —$C(O)R^a$, —$C(O)OR^a$, —$C(O)NR^bR^c$, —$OC(O)NR^bR^c$, —$NR^bC(O)OR^a$, —$SR^a$, —$S(O)_{1-2}R^a$, —$S(O)_2F$, —$S(O)_2NR^bR^c$, —$NR^bS(O)_2R^a$, —$N_3$, —CN or —$NO_2$, wherein each $C_{1-6}$ alkyl, $C_{1-6}$ heteroalkyl, aryl or heteroaryl is optionally substituted with 1, 2, 3, 4 or 5 halogen, —$OR^a$, —$C(O)R^a$, —$C(O)OR^a$, —$C(O)NR^bR^c$, —$OC(O)NR^bR^c$, —$NR^bC(O)OR^a$, —$SR^a$, —$S(O)_{1-2}R^a$, —$S(O)_2F$, —$S(O)_2NR^bR^c$, —$NR^bS(O)_2R^a$, —$N_3$, —CN or —$NO_2$ groups, which may be the same or different;
each $R^a$ is independently —H, $C_{1-6}$ alkyl, $C_{1-6}$ haloalkyl, $C_{1-6}$ heteroalkyl, aryl or heteroaryl, wherein each aryl or heteroaryl is optionally substituted with 1, 2, 3, 4 or 5 $R^{21}$ groups, which may be the same or different;
$R^b$ and $R^c$ are each independently —H, —$NH_2$, $C_{1-6}$ alkyl, $C_{1-6}$ heteroalkyl, aryl or heteroaryl, wherein each $C_{1-6}$ alkyl, $C_{1-6}$ heteroalkyl, aryl or heteroaryl is optionally substituted with 1, 2, 3, 4 or 5 $R^{21}$ groups; or $R^b$ and $R^c$ together with the atoms to which they are attached form a $C_{1-10}$ heterocycloalkyl;
$R^{21}$ is $C_{1-6}$ alkyl, —CN, aryl, heteroaryl or halogen.

In certain embodiments, the current disclosure relates to a pharmaceutical composition comprising a compound of Formula (I), or a pharmaceutically acceptable salt thereof, and a pharmaceutically acceptable carrier.

In certain embodiments, the current disclosure relates to an article of manufacture comprising a unit dosage of a compound of Formula (I), or a pharmaceutically acceptable salt thereof.

In certain embodiments, the current disclosure relates to a method of inhibiting reverse transcriptase in a subject in need thereof, comprising administering a compound of Formula (I), or a pharmaceutically acceptable salt thereof, to the subject.

In certain embodiments, the current disclosure relates to a method for treating or preventing an HIV infection in a subject in need thereof, comprising administering to the subject a compound of Formula (I), or a pharmaceutically acceptable salt thereof.

In certain embodiments, the current disclosure relates to a method for preventing an HIV infection in a subject, comprising administering to the subject a compound of Formula (I), or a pharmaceutically acceptable salt thereof. In certain embodiments, the subject is at risk of contracting the HIV virus, such as a subject who has one or more risk factors known to be associated with contracting the HIV virus.

In certain embodiments, the current disclosure relates to a method for treating or preventing an HIV infection in a subject in need thereof, comprising administering to the subject a compound of Formula (I), or a pharmaceutically acceptable salt thereof, in combination with a therapeutically effective amount of one or more additional therapeutic agents.

In certain embodiments, the current disclosure relates to a compound of Formula (I), or a pharmaceutically acceptable salt thereof, for use in medical therapy.

In certain embodiments, the current disclosure relates to a compound of Formula (I), or a pharmaceutically acceptable salt thereof, for use in treating or preventing an HIV virus infection in a subject.

In certain embodiments, the current disclosure relates to the use of a compound of Formula (I), or a pharmaceutically acceptable salt thereof, for the manufacture of a medicament for treating or preventing an HIV virus infection in a subject.

Additional embodiments of the present disclosure are disclosed herein.

DETAILED DESCRIPTION

The description below is made with the understanding that the present disclosure is to be considered as an exemplification of the claimed subject matter, and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

Unless defined otherwise, all technical and scientific terms used herein have the same meaning as commonly understood by one of ordinary skill in the art. A dash at the front or end of a chemical group is a matter of convenience to indicate the point of attachment to a parent moiety; chemical groups may be depicted with or without one or more dashes without losing their ordinary meaning. A wavy line drawn through a line in a chemical structure or a dashed line drawn through a line in a chemical structure indicates a point of attachment of a group. A dashed line within a chemical structure indicates an optional bond. A prefix such as "$C_{u-v}$" or ($C_u$-$C_v$) indicates that the following group has from u to v carbon atoms. For example, "$C_{1-6}$alkyl" indicates that the alkyl group has from 1 to 6 carbon atoms.

When trade names are used herein, it is intended to independently include the tradename product and the active pharmaceutical ingredient(s) of the tradename product.

As used herein and in the appended claims, the singular forms "a" and "an", and "the" include plural referents unless the context clearly dictates otherwise. Thus, e.g., reference to "the compound" includes a plurality of such compounds and reference to "the assay" includes reference to one or more assays, and so forth.

"Alkyl" as used herein is a linear or branched saturated monovalent hydrocarbon. For example, an alkyl group can have 1 to 20 carbon atoms (i.e., ($C_{1-20}$)alkyl) or an alkyl group can have 1 to 10 carbon atoms (i.e., ($C_{1-10}$)alkyl), or an alkyl group can have 1 to 8 carbon atoms (i.e., ($C_{1-8}$) alkyl), or 1 to 6 carbon atoms (i.e., ($C_{1-6}$ alkyl), or 1 to 4 carbon atoms (i.e., ($C_{1-4}$)alkyl). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), and octyl (—$(CH_2)_7CH_3$).

The term "aryl" as used herein refers to a single all carbon aromatic ring or a multiple condensed all carbon ring system wherein at least one of the rings is aromatic. For example, in certain embodiments, an aryl group has 6 to 20 annular carbon atoms, 6 to 14 annular carbon atoms, or 6 to 12 annular carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, Spiro and bridged bonds when allowed by valency requirements. It is also to be understood that when reference is made to a certain atom-range membered aryl (e.g., 6-12 membered aryl), the atom range is for the total ring (annular) atoms of the aryl. For example, a 6-membered aryl would include phenyl and a 10-membered aryl would include naphthyl and 1, 2, 3, 4-tetrahydronaphthyl. Non-limiting examples of aryl groups include, but are not limited to, phenyl, indenyl, naphthyl, 1, 2, 3, 4-tetrahydronaphthyl, anthracenyl, and the like.

"Arylalkyl" refers to an alkyl radical as defined herein in which one of the hydrogen atoms bonded to a carbon atom is replaced with an aryl radical as described herein (i.e., an aryl-alkyl-moiety). The alkyl group of the "arylalkyl" includes alkyl groups that are 1 to 6 carbon atoms (i.e. aryl($C_1$-$C_6$)alkyl). Arylalkyl groups include, but are not limited to, benzyl, 2-phenylethan-1-yl, 1-phenylpropan-1-yl, naphthylmethyl, 2-naphthylethan-1-yl and the like.

"Boronic acid" refers to the group —$B(OH)_2$.

"Boronic acid ester" refers to an ester derivative of a boronic acid compound. Suitable boronic acid ester derivatives include those of the formula —$B(OR)_2$ where each R is independently alkyl, aryl, arylalkyl, heteroalkyl, or heteroaryl. Additionally, the two R groups of —$B(OR)_2$ may be taken together to form a cyclic ester, e.g. having the structure

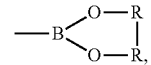

where each R may be the same or different. Examples of boronic acid ester include boronic acid pinacol ester and boronic acid catechol ester.

"Cycloalkyl" refers to a single saturated or partially unsaturated all carbon ring having 3 to 20 annular carbon atoms (i.e., $C_3$-$C_{20}$ cycloalkyl), for example from 3 to 12 annular atoms, for example from 3 to 10 annular atoms. The term "cycloalkyl" also includes multiple condensed, saturated and partially unsaturated all carbon ring systems (e.g., ring systems comprising 2, 3 or 4 carbocyclic rings). Accordingly, cycloalkyl includes multicyclic carbocycles such as a bicyclic carbocycles (e.g., bicyclic carbocycles having about 6 to 12 annular carbon atoms such as bicyclo [3.1.0]hexane and bicyclo[2.1.1]hexane), and polycyclic carbocycles (e.g., tricyclic and tetracyclic carbocycles with up to about 20 annular carbon atoms). The rings of a multiple condensed ring system can be connected to each other via fused, Spiro and bridged bonds when allowed by valency requirements. Non-limiting examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

"Halo" or "halogen" refers to fluoro, chloro, bromo and iodo.

"Haloalkyl" refers to substitution of alkyl groups with 1, 2, 3, 4 or 5 or, in some embodiments, 1, 2 or 3 halogen groups, e.g., —CH$_2$Cl, —CH$_2$F, —CH$_2$Br, —CFClBr, —CH$_2$CH$_2$Cl, —CH$_2$CH$_2$F, —CF$_3$, —CH$_2$CF$_3$, —CH$_2$CCl$_3$, and the like, and further includes those alkyl groups such as perfluoroalkyl in which all hydrogen atoms are replaced by fluorine atoms.

The term "heteroalkyl" as used herein refers to an alkyl as defined herein, wherein one or more of the carbon atoms of the alkyl are replaced by an O, S, or NR$^q$, (or if the carbon atom being replaced is a terminal carbon with an OH, SH or N(R$^q$)$_2$) wherein each R$^q$ is independently H or (C$_1$-C$_6$) alkyl. For example, (C$_1$-C$_8$)heteroalkyl intends a heteroalkyl wherein one or more carbon atoms of a C$_1$-C$_8$ alkyl is replaced by a heteroatom (e.g., O, S, NR$^q$, OH, SH or N(R$^q$)$_2$), which may the same or different. Examples of heteroalkyls include but are not limited to methoxymethyl, ethoxymethyl, methoxy, 2-hydroxyethyl and N,N'-dimethylpropylamine. A heteroatom of a heteroalkyl may optionally be oxidized or alkylated. A heteroatom may be placed at any interior position of the heteroalkyl group or at a position at which the group is attached to the remainder of the molecule. Examples include, but are not limited to, —CH$_2$OCH$_3$, —CH$_2$CH$_2$NHCH$_3$, —CH$_2$CH$_2$N(CH$_3$)—CH$_3$, —CH$_2$SCH$_2$CH$_3$, —S(O)CH$_3$, —CH$_2$CH$_2$S(O)$_2$CH$_3$, —CH$_2$CH$_2$OCH$_3$, —CHCHN(CH$_3$)CH$_3$, —CH$_2$NHOCH$_3$ and —CH$_2$OC(CH$_3$)$_3$.

The term "heteroaryl" as used herein refers to a single aromatic ring that has at least one atom other than carbon in the ring, wherein the atom is selected from the group consisting of oxygen, nitrogen and sulfur; the term also includes multiple condensed ring systems that have at least one such aromatic ring, which multiple condensed ring systems are further described below. Thus, the term includes single aromatic rings of from about 1 to 6 annular carbon atoms and about 1-4 annular heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g., ring systems comprising 2, 3 or 4 rings) wherein a heteroaryl group, as defined above, can be condensed with one or more rings selected from heteroaryls (to form for example a naphthyridinyl such as 1,8-naphthyridinyl), heterocycloalkyls, (to form for example a 1, 2, 3, 4-tetrahydronaphthyridinyl such as 1, 2, 3, 4-tetrahydro-1, 8-naphthyridinyl), cycloalkyls (to form for example 5,6,7, 8-tetrahydroquinolyl) and aryls (to form for example indazolyl) to form the multiple condensed ring system. Thus, a heteroaryl (a single aromatic ring or multiple condensed ring system) has about 1-20 annular carbon atoms and about 1-6 annular heteroatoms. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system and at any suitable atom of the multiple condensed ring system including a carbon atom and heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl and thianaphthenyl.

"Heterocycloalkyl" or "heterocyclyl" as used herein refers to a single saturated or partially unsaturated non-aromatic ring or a non-aromatic multiple ring system that has at least one heteroatom in the ring (at least one annular heteroatom selected from oxygen, nitrogen, and sulfur). Unless otherwise specified, a heterocycloalkyl group has from 5 to about 20 annular atoms, for example from 5 to 14 annular atoms, for example from 5 to 10 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. The term also includes single saturated or partially unsaturated rings (e.g., 5, 6, 7, 8, 9, or 10-membered rings) having from about 4 to 9 annular carbon atoms and from about 1 to 3 annular heteroatoms selected from the group consisting of oxygen, nitrogen and sulfur in the ring. The rings of the multiple condensed ring system can be connected to each other via fused, spiro and bridged bonds when allowed by valency requirements. Heterocycloalkyl groups include, but are not limited to, azetidine, aziridine, imidazolidine, imino-oxoimidazolidine, morpholine, oxirane (epoxide), oxetane, piperazine, piperidine, pyrazolidine, piperidine, pyrrolidine, pyrrolidinone, tetrahydrofuran, tetrahydrothiophene, dihydropyridine, tetrahydropyridine, quinuclidine, N-bromopyrrolidine, N-chloropiperidine, and the like.

"Hydroxy" or "hydroxyl" refers to the group —OH.

"Oxo" refers to a double-bonded oxygen (=O). In compounds where an oxo group is bound to an sp$^2$ nitrogen atom, an N-oxide is indicated.

It is understood that combinations of chemical groups may be used and will be recognized by persons of ordinary skill in the art. For instance, the group "hydroxyalkyl" would refer to a hydroxyl group attached to an alkyl group.

The terms "optional" or "optionally" mean that the subsequently described event or circumstance may but need not occur, and that the description includes instances where the event or circumstance occurs and instances in which it does not.

"Tautomers" as used herein refers to isomers of a compound that differ from each other in the position of a proton and/or in electronic distribution. Thus, both proton migration tautomers and valence tautomers are intended and described and it is understood that more than two tautomers may exist for a given compound. Examples of tautomers include, but are not limited to, enol-keto tautomers:

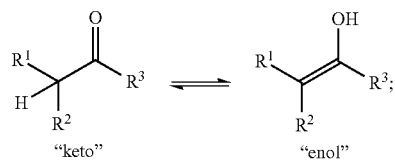

imine-enamine tautomers:

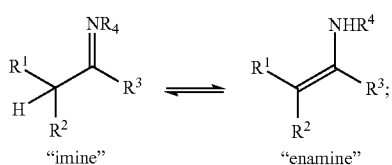

lactam-lactim tautomers:

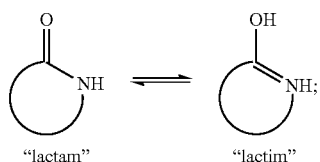

amide-imidic acid tautomers:

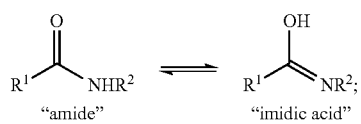

amino-imine tautomers:

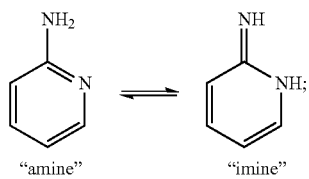 [SMILES: Nc1ccccn1 ; N=c1cccc[nH]1]

and tautomeric forms of heteroaryl groups containing a ring atom attached to both a ring —NH— moiety and a ring =N— moiety such as present in pyrazoles, imidazoles, benzimidazoles, triazoles and tetrazoles (see, e.g., Smith, March's Advanced Organic Chemistry ($5^{th}$ ed.), pp. 1218-1223, Wiley-Interscience, 2001; Katritzky A. and Elguero J, et al., The Tautomerism of Heterocycles, Academic Press (1976)).

"Pharmaceutically acceptable" refers to compounds, salts, compositions, dosage forms and other materials which are useful in preparing a pharmaceutical composition that is suitable for veterinary or human pharmaceutical use.

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-napththalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion (e.g. a sodium or potassium), an alkaline earth ion (e.g. calcium or magnesium), or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, Pa., (2005), at p. 732, Table 38-5, both of which are hereby incorporated by reference herein.

"Subject" and "subjects" refers to humans, domestic animals (e.g., dogs and cats), farm animals (e.g., cattle, horses, sheep, goats and pigs), laboratory animals (e.g., mice, rats, hamsters, guinea pigs, pigs, rabbits, dogs, and monkeys), and the like.

As used herein, "treatment" or "treating" is an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

As used herein, "delaying" development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition. For example, a method that "delays" development of AIDS is a method that reduces the probability of disease development in a given time frame and/or reduces extent of the disease in a given time frame, when compared to not using the method. Such comparisons may be based on clinical studies, using a statistically significant number of subjects. For example, the development of AIDS can be detected using known methods, such as confirming an individual's $HIV^+$ status and assessing the individual's T-cell count or other indication of AIDS development, such as extreme fatigue, weight loss, persistent diarrhea, high fever, swollen lymph nodes in the neck, armpits or groin, or presence of an opportunistic condition that is known to be associated with AIDS (e.g., a condition that is generally not present in individuals with functioning immune systems but does occur in AIDS patients). Development may also refer to disease progression that may be initially undetectable and includes occurrence, recurrence and onset.

As used herein, "prevention" or "preventing" refers to a regimen that protects against the onset of the disease or disorder such that the clinical symptoms of the disease do not develop. Thus, "prevention" relates to administration of a therapy (e.g., administration of a therapeutic substance) to a subject before signs of the disease are detectable in the subject (e.g., administration of a therapeutic substance to an subject in the absence of detectable infectious agent (e.g., virus) in the subject). The subject may be an individual at risk of developing the disease or disorder, such as an individual who has one or more risk factors known to be associated with development or onset of the disease or disorder. Thus, the term "preventing HIV infection" refers to administering to a subject who does not have a detectable HIV infection an anti-HIV therapeutic substance. It is understood that the subject for anti-HIV preventative therapy may be an individual at risk of contracting the HIV virus.

As used herein, an "at risk" individual is an individual who is at risk of developing a condition to be treated. An individual "at risk" may or may not have detectable disease or condition, and may or may not have displayed detectable disease prior to the treatment of methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). For example, individuals at risk for AIDS are those having HIV.

As used herein, the term "effective amount" refers to an amount that is effective to elicit the desired biological or medical response, including the amount of a compound that, when administered to a subject for treating a disease, is sufficient to effect such treatment for the disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

Except as expressly defined otherwise, the present disclosure includes all tautomers of compounds detailed herein, even if only one tautomer is expressly represented (e.g., both tautomeric forms are intended and described by the presentation of one tautomeric form where a pair of two tautomers may exist). For example, if reference is made to a compound containing a lactam (e.g., by structure or chemical name), it is understood that the corresponding lactim tautomer is included by this disclosure and described the same as if the lactim were expressly recited either alone or together with the lactam. Where more than two tautomers may exist, the present disclosure includes all such tautuomers even if only a single tautomeric form is depicted by chemical name and/or structure.

Compositions detailed herein may comprise a compound of the present disclosure in a racemic or non-racemic mixture of stereoisomers or may comprise a compound of the present disclosure as a substantially pure isomer. Stereoisomers include enantiomers and diastereomers. The compounds may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see, e.g., Chapter 4 of Advanced Organic Chemistry, 4th ed., J. March, John Wiley and Sons, New York, 1992).

It is understood by one skilled in the art that this disclosure also includes any compound disclosed herein that may be enriched at any or all atoms above naturally occurring isotopic ratios with one or more isotopes such as, but not limited to, deuterium ($^2$H or D).

Disclosed are also compounds in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Compounds of a given formula described herein encompasses the compound disclosed and all pharmaceutically acceptable salts, esters, stereoisomers, tautomers, prodrugs, solvates, and deuterated forms thereof, unless otherwise specified.

Depending on the particular substituents, the compounds of Formula I may exist in tautomeric forms. It is understood that two or more tautomeric forms may exist for a given compound structure. For example, a compound of Formula I (where $R^2$ is —OH) may exist in at least the following tautomeric forms:

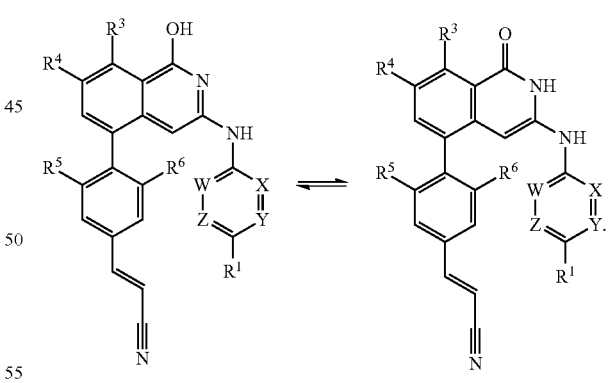

As is understood by those of skill in the art, various other tautomeric forms may exist and are intended to be encompassed by the compounds of Formula I. Some descriptions herein expressly refer to "tautomers thereof" but it is understood that, even in the absence of such language, tautomers are intended and described. Further, it is understood that the compounds of Formula I may shift between various tautomeric forms or exist in various ratios of each form based on the particular environment of the compound.

The compounds disclosed herein may contain chiral centers, which may be either of the (R) or (S) configuration, or which may comprise a mixture thereof. Accordingly, the present disclosure includes stereoisomers of the compounds described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds of the present disclosure.

The compounds of the present disclosure may be compounds according to Formula (I) with one or more chiral centers, which may be either of the (R) or (S) configuration, or which may comprise a mixture thereof.

The present disclosure includes both racemic mixtures of a compound of formula I and isolated isomers of Formula (I) or any variation thereof. Where more than one chiral center is present in a compound of the present disclosure, some, none, or all of the chiral centers may be enantiomerically enriched. Thus, mixtures of a compound of Formula (I) may be racemic with respect to one or more chiral centers and/or enantiomerically enriched with respect to one or more chiral centers.

The present disclosure relates to a compound of formula (I)

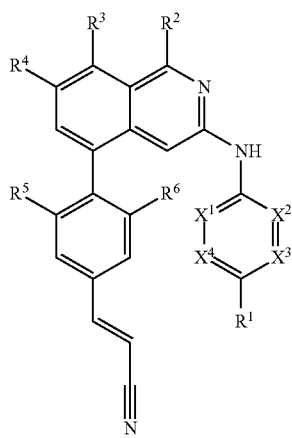

(I)

or a tautomer or pharmaceutically acceptable salt thereof, wherein $X^1$, $X^2$, $X^3$, and $X^4$ are each independently $C(R^7)$ or N, wherein 0 to 2 of $X^1$, $X^2$, $X^3$, and $X^4$ are N;

$R^1$ is —H, —CN, —OR$^a$, $C_{1-6}$ haloalkyl or halogen;

$R^2$ is —H, —NR$^b$R$^c$, —SR$^a$, —OR$^a$ or $C_{1-6}$ alkyl, wherein $C_{1-6}$ alkyl is optionally substituted with 1, 2, 3, 4 or 5 $R^8$ groups, which may be the same or different;

$R^3$ and $R^4$ are each independently —H, —OR$^a$, halogen, —NR$^b$R$^c$, —C(O)OR$^a$, —CN, —C(O)NR$^b$R$^c$, —NHC(O)NR$^b$R$^c$, —OC(O)NR$^b$R$^c$, $CH_2C(O)NR^bR^c$, $C_{1-6}$ alkyl or $C_{1-6}$ heteroalkyl, wherein each $C_{1-6}$ alkyl or $C_{1-6}$ heteroalkyl is optionally substituted with 1, 2, 3, 4 or 5 $R^8$ groups, which may be the same or different;

$R^5$ and $R^6$ are each independently halogen, —OR$^a$ or $C_{1-6}$ alkyl, wherein each $C_{1-6}$ alkyl is optionally substituted with 1, 2, 3, 4 or 5 $R^8$ groups, which may be the same or different;

each $R^7$ is independently —H, halogen, —OR$^a$ or $C_{1-6}$ alkyl, wherein each $C_{1-6}$ alkyl is optionally substituted with 1, 2, 3, 4 or 5 $R^8$ groups, which may be the same or different;

each $R^8$ is independently $C_{1-6}$ alkyl, $C_{1-6}$ heteroalkyl, aryl, heteroaryl, halogen, —OR$^a$, —C(O)R$^a$, —C(O)OR$^a$, —C(O)NR$^b$R$^c$, —OC(O)NR$^b$R$^c$, —NR$^b$C(O)OR$^a$, —S(O)$_{1-2}$R$^a$, —S(O)$_2$F, —S(O)$_2$NR$^b$R$^c$, —NR$^b$S(O)$_2$R$^a$, —N$_3$, —CN or —NO$_2$, wherein each $C_{1-6}$ alkyl, $C_{1-6}$ heteroalkyl, aryl or heteroaryl is optionally substituted with 1, 2, 3, 4 or 5 halogen, —OR$^a$, —C(O)R$^a$, —C(O)OR$^a$, —C(O)NR$^b$R$^c$, —OC(O)NR$^b$R$^c$, —NR$^b$C(O)OR$^a$, —SR$^a$, —S(O)$_{1-2}$R$^a$, —S(O)$_2$F, —S(O)$_2$NR$^b$R$^c$, —NR$^b$S(O)$_2$R$^a$, —N$_3$, —CN or —NO$_2$ groups, which may be the same or different;

each $R^a$ is independently —H, $C_{1-6}$ alkyl, $C_{1-6}$ haloalkyl, $C_{1-6}$ heteroalkyl, aryl or heteroaryl, wherein each aryl or heteroaryl is optionally substituted with 1, 2, 3, 4 or 5 $R^{21}$ groups, which may be the same or different;

$R^b$ and $R^c$ are each independently —H, —NH$_2$, $C_{1-6}$ alkyl, $C_{1-6}$ heteroalkyl, aryl or heteroaryl, wherein each $C_{1-6}$ alkyl, $C_{1-6}$ heteroalkyl, aryl or heteroaryl is optionally substituted with 1, 2, 3, 4 or 5 $R^{21}$ groups; or $R^b$ and $R^c$ together with the atoms to which they are attached form a $C_{1-10}$ heterocycloalkyl;

$R^{21}$ is $C_{1-6}$ alkyl, —CN, aryl, heteroaryl or halogen.

In certain embodiments in formula (I), $R^2$ is —H, —NR$^b$R$^c$ or —OH.

In certain embodiments in formula (I), $R^2$ is —H, —NH$_2$ or —OH.

In certain embodiments in formula (I), $R^2$ is —NH$_2$. In certain embodiments, $R^2$ is —H.

In certain embodiments in formula (I), $R^3$ and $R^4$ are each independently —H, —OR$^a$, halogen, —NR$^b$R$^c$, —C(O)OR$^c$, or —C(O)NR$^b$R$^c$. In certain embodiments in formula (I), $R^3$ and $R^4$ are each independently —H, C(O)OR$^a$ or —C(O)NR$^b$R$^c$.

In certain embodiments in formula (I), $R^3$ and $R^4$ are each —H.

In one variation, the present disclosure relates to compounds of formula (Ia), which are compounds of formula (I):

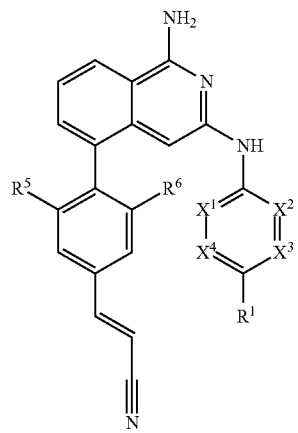

(Ia)

or a tautomer or pharmaceutically acceptable salt thereof.
In certain embodiments in formula (I) and (Ia),

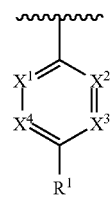

is selected from

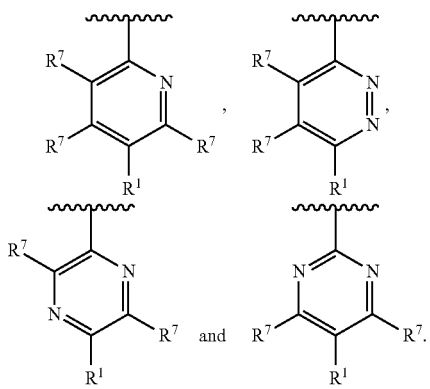

In certain embodiments in formula (I) and (Ia),

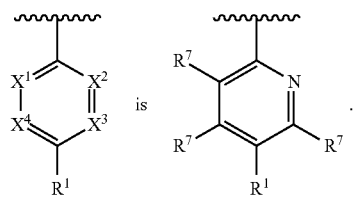

In certain embodiments,

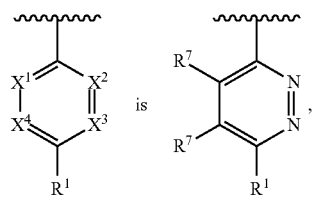

In certain embodiments,

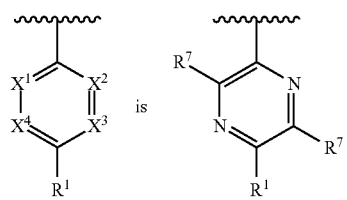

In certain embodiments,

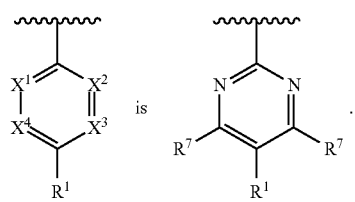

In one variation, the present disclosure relates to compounds of formula (Ib), which are compounds of formula (I):

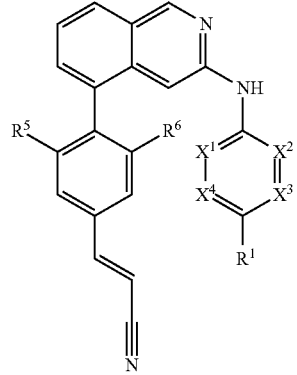

or a tautomer or pharmaceutically acceptable salt thereof.

In certain embodiments in formula (I) and (Ib),

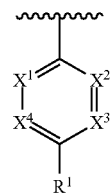

is selected from

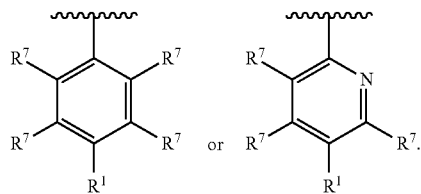

In certain embodiments in formula (I) and (Ib),

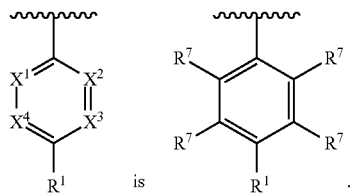

In certain embodiments,

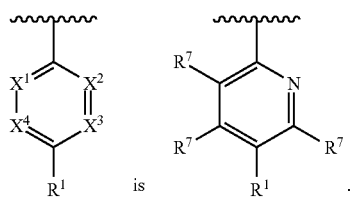

In certain embodiments in formula (I), (Ia), and (Ib), $R^5$ and $R^6$ are each independently halogen, —O—$C_{1-6}$ alkyl or $C_{1-6}$ alkyl, wherein each $C_{1-6}$ alkyl is optionally substituted with 1, 2, 3, 4 or 5 $R^8$ groups, which may be the same or different.

In certain embodiments in formula (I), (Ia), and (Ib), $R^5$ and $R^6$ are each independently $C_{1-3}$ alkyl.

In certain embodiments in formula (I), (Ia), and (Ib), $R^5$ and $R^6$ are each independently —$CH_3$.

In certain embodiments in formula (I), (Ia), and (Ib), $R^1$ is —H, —CN, —O—$C_{1-6}$ alkyl, —$CF_3$, —O—$C_{1-3}$ haloalkyl or halogen.

In certain embodiments in formula (I), (Ia), and (Ib), $R^1$—CN.

In certain embodiments in formula (I), (Ia), and (Ib), each $R^7$ is independently —H, halogen, —O—$C_{1-6}$ alkyl or $C_{1-6}$ alkyl, wherein each $C_{1-6}$ alkyl is optionally substituted with 1, 2, 3, 4 or 5 $R^8$ groups, which may be the same or different.

In certain embodiments in formula (I), (Ia), and (Ib), each $R^7$ is independently —H or $C_{1-3}$ alkyl.

In certain embodiments in formula (I), (Ia), and (Ib), each $R^7$ is —H.

It is understood that any variable for

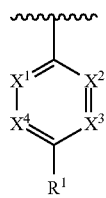

of formula (I), (Ia) and (Ib), may be combined with any variable of $R^2$ in formula (I), (Ia) and (Ib), the same as if each and every combination were specifically and individually listed. For example, in one variation of formula (I), (Ia) and (Ib),

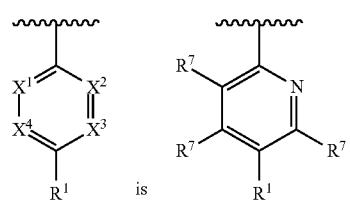

and $R^2$ is —$NH_2$. In another variation,

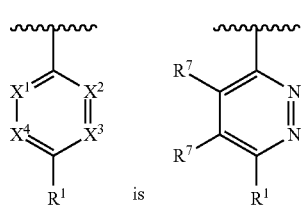

and $R^2$ is —$NH_2$. In another variation,

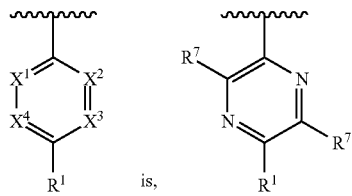

and $R^2$ is —$NH_2$. In another variation,

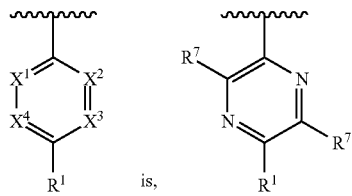

and $R^2$ is —$NH_2$. In another variation,

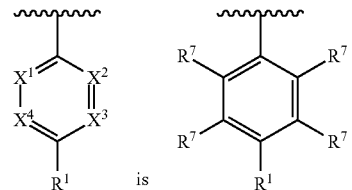

and $R^2$ is —H. In another variation,

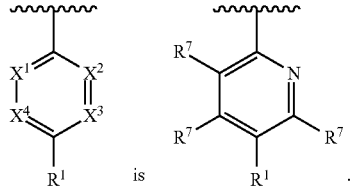

and $R^2$ is —$NH_2$. In another variation,

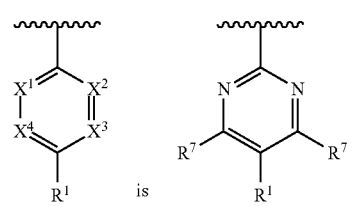

and $R^2$ is —H.

It is understood that any variable for $R^5$ of formula (I), (Ia) and (Ib), may be combined with any variable of $R^2$ in formula (I), (Ia) and (Ib), the same as if each and every combination were specifically and individually listed. For example, in one variation of formula (I), (Ia) and (Ib), $R^5$ is methyl and $R^2$ is —$NH_2$. In another variation, $R^5$ is methyl and $R^2$ is —H.

It is understood that any variable for $R^6$ of formula (I), (Ia) and (Ib), may be combined with any variable of $R^2$ in formula (I), (Ia) and (Ib), the same as if each and every combination were specifically and individually listed. For example, in one variation of formula (I), (Ia) and (Ib), $R^6$ is methyl and $R^2$ is —$NH_2$. In another variation, $R^6$ is methyl and $R^2$ is —H.

It is understood that any variable for $R^3$ of formula (I), (Ia) and (Ib), may be combined with any variable of $R^2$ in formula (I), (Ia) and (Ib), the same as if each and every combination were specifically and individually listed. For example, in one variation of formula (I), (Ia) and (Ib), $R^3$ is —H and $R^2$ is —$NH_2$. In another variation, $R^3$ is —H and $R^2$ is —H.

It is understood that any variable for R⁴ of formula (I), (Ia) and (Ib), may be combined with any variable of R² in formula (I), (Ia) and (Ib), the same as if each and every combination were specifically and individually listed. For example, in one variation of formula (I), (Ia) and (Ib), R⁴ is —H and R² is —NH₂. In another variation, R⁴ is —H and R² is —H.

It is understood that any variable for R¹ of formula (I), (Ia) and (Ib), may be combined with any variable of R² in formula (I), (Ia) and (Ib), the same as if each and every combination were specifically and individually listed. For example, in one variation of formula (I), (Ia) and (Ib), R¹ is —CN and R² is —NH₂. In another variation, R¹ is CN and R² is —H.

In certain embodiments of formula (I), (Ia) and (Ib), where R² is —NH₂, the compounds may have any one or more of the following structural features:

a)

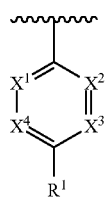

is selected from

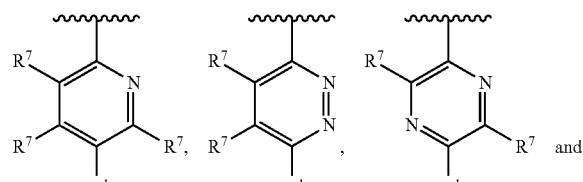

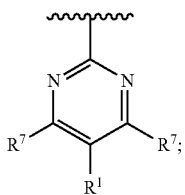

b) R³ and R⁴ are each —H;
c) R⁵ and R⁶ are each independently —CH₃; and
d) R¹—CN.

In one variation, the compounds conform to at least one of features (a)-(d). In another variation, the compounds conform to two or more (and in certain variations, all) of features (a)-(d). In a particular variation, the compounds conform to feature (a). In another variation, the compounds conform to features (a) and (b). In another variation, the compounds conform to features (a) and (c). In another variation, the compounds conform to features (a) and (d).

In certain embodiments of formula (I), (Ia) and (Ib), where R² is —H, the compounds may have any one or more of the following structural features:

a)

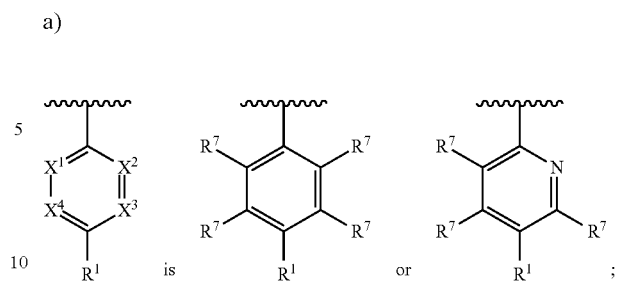

b) R³ and R⁴ are each —H;
c) R⁵ and R⁶ are each independently —CH₃; and
d) R¹—CN.

In one variation, the compounds conform to at least one of features (a)-(d). In another variation, the compounds conform to two or more (and in certain variations, all) of features (a)-(d). In a particular variation, the compounds conform to feature (a). In another variation, the compounds conform to features (a) and (b). In another variation, the compounds conform to features (a) and (c). In another variation, the compounds conform to features (a) and (d).

The present disclosure relates to the following compounds or a pharmaceutically acceptable salt thereof.

| Structure | Compound ID |
|---|---|
| (structure) | 3 |
| (structure) | 4 |
| (structure) | 5 |

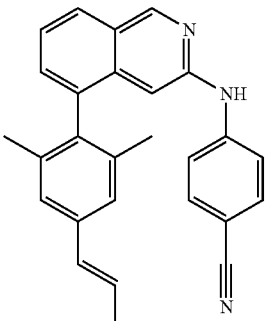

Pharmaceutical Compositions

Pharmaceutical compositions comprising the compounds disclosed herein, or pharmaceutically acceptable salts thereof, may be prepared with conventional carriers (e.g., inactive ingredient or excipient material) which may be selected in accord with ordinary practice. Tablets may contain excipients including glidants, fillers, binders and the like. Aqueous compositions may be prepared in sterile form, and when intended for delivery by other than oral administration generally may be isotonic. All compositions may optionally contain excipients such as those set forth in the Rowe et al, Handbook of Pharmaceutical Excipients, 5$^{th}$ edition, American Pharmacists Association, 1986. Excipients can include ascorbic acid and other antioxidants, chelating agents such as EDTA, carbohydrates such as dextrin, hydroxyalkylcellulose, hydroxyalkylmethylcellulose, stearic acid and the like. In certain embodiments, the composition is disclosed as a solid dosage form, including a solid oral dosage form. The pH of a composition may range from about 3 to about 11, but is ordinarily about 7 to 10.

While it is possible for the active ingredients to be administered alone, it may be preferable to present them as pharmaceutical compositions. The compositions, both for veterinary and for human use, comprise at least one compound of formula (I), together with one or more acceptable carriers and optionally other therapeutic ingredients. In one embodiment, the pharmaceutical composition comprises a compound of formula (I), or a tautomer or a pharmaceutically acceptable salt thereof, a pharmaceutically acceptable carrier and one other therapeutic ingredient. The carrier(s) are "acceptable" in the sense of being compatible with the other ingredients of the composition and physiologically innocuous to the recipient thereof.

The compositions include those suitable for various administration routes, including oral administration. The compositions may conveniently be presented in unit dosage form and may be prepared by any of the methods well known in the art of pharmacy. Such methods include the step of bringing into association the active ingredient (e.g., a compound of formula (I) or a pharmaceutical salt thereof) with one or more inactive ingredients (e.g., a carrier, pharmaceutical excipient, etc.). The compositions may be prepared by uniformly and intimately bringing into association the active ingredient with liquid carriers or finely divided solid carriers or both, and then, if necessary, shaping the product. Techniques and formulations generally are found in Remington: The Science and Practice of Pharmacy, 21$^{st}$ Edition, Lippincott Wiliams and Wilkins, Philadelphia, Pa., 2006.

Compositions described herein that are suitable for oral administration may be presented as discrete units (a unit dosage form) including but not limited to capsules, cachets or tablets each containing a predetermined amount of the active ingredient.

Pharmaceutical compositions disclosed herein comprise one or more compounds disclosed herein, or a pharmaceutically acceptable salt thereof, together with one or more pharmaceutically acceptable carriers or excipients and optionally other therapeutic agents. Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that may be combined with the inactive ingredients to produce a dosage form may vary depending upon the intended treatment subject and the particular mode of administration. For example, in some embodiments, a dosage form for oral administration to humans may contain approximately 1 to 1000 mg of active material formulated with an appropriate and convenient amount of carrier material (e.g., inactive ingredient or excipient material). In certain embodiments, the carrier material varies from about 5 to about 95% of the total compositions (weight:weight).

It should be understood that in addition to the ingredients particularly mentioned above the compositions of these embodiments may include other agents conventional in the art having regard to the type of composition in question, for example those suitable for oral administration may include flavoring agents.

In certain embodiments, a composition comprising an active ingredient disclosed herein (a compound of formula (I) or a pharmaceutically acceptable salt thereof) in one variation does not contain an agent that affects the rate at which the active ingredient is metabolized. Thus, it is understood that compositions comprising a compound of formula (I) in certain embodiments do not comprise an agent that would affect (e.g., slow, hinder or retard) the metabolism of a compound of formula (I) or any other active ingredient administered separately, sequentially or simultaneously with a compound of formula (I). It is also understood that any of the methods, kits, articles of manufacture and the like detailed herein in certain embodiments do not comprise an agent that would affect (e.g., slow, hinder or retard) the metabolism of a compound of formula (I) or any other active ingredient administered separately, sequentially or simultaneously with a compound of any one of formula (I).

Methods of Use

Disclosed herein is a method of inhibiting an HIV reverse transcriptase in an individual in need thereof, comprising administering a compound of Formula (I), or a pharmaceutically acceptable salt thereof, to the individual. In certain embodiments, the individual in need thereof is a human who has been infected with HIV. In certain embodiments, the individual in need thereof is a human who has been infected with HIV but who has not developed AIDS. In certain embodiments, the individual in need thereof is an individual at risk for developing AIDS. In certain embodiments, the individual in need thereof is a human who has been infected with HIV and who has developed AIDS. In certain embodiments of the methods disclosed herein, a compound of Formula (I), or a pharmaceutically acceptable salt thereof, is administered to the individual separately, sequentially or simultaneously with another active ingredient for treating HIV, such as HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof.

In certain embodiments, a method for treating or preventing an HIV viral infection in an individual (e.g., a human), comprising administering a compound of formula (I), or a pharmaceutically acceptable salt thereof, to the individual is disclosed.

In certain embodiments, a method for inhibiting the replication of the HIV virus, treating AIDS or delaying the onset of AIDS in an individual (e.g., a human), comprising administering a compound of any formula (I), or a pharmaceutically acceptable salt thereof, to the individual is disclosed.

In certain embodiments, a method for preventing an HIV infection in an individual (e.g., a human), comprising administering a compound of formula (I), or a pharmaceutically acceptable salt thereof, to the individual is disclosed. In certain embodiments, the individual is at risk of contracting the HIV virus, such as an individual who has one or more risk factors known to be associated with contracting the HIV virus.

In certain embodiments, a method for treating an HIV infection in an individual (e.g., a human), comprising administering a compound of formula (I), or a pharmaceutically acceptable salt thereof, to the individual is disclosed.

In certain embodiments, a method for treating an HIV infection in an individual (e.g., a human), comprising administering to the individual in need thereof a therapeutically effective amount of a compound of formula (I), or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof is disclosed.

In certain embodiments, a compound of formula (I), or a pharmaceutically acceptable salt thereof for use in medical therapy of an HIV viral infection (e.g. HIV-1 or the replication of the HIV virus (e.g. HIV-1) or AIDS or delaying the onset of AIDS in an individual (e.g., a human)) is disclosed.

In certain embodiments, a compound of any of formula (I), or a pharmaceutically acceptable salt thereof for use in the manufacture of a medicament for treating an HIV viral infection or the replication of the HIV virus or AIDS or delaying the onset of AIDS in an individual (e.g., a human) is disclosed. One embodiment relates to a compound of formula (I), or a pharmaceutically acceptable salt thereof, for use in the prophylactic or therapeutic treatment of an HIV infection or AIDS or for use in the therapeutic treatment or delaying the onset of AIDS is disclosed.

In certain embodiments, the use of a compound of formula (I), or a pharmaceutically acceptable salt thereof, for the manufacture of a medicament for an HIV virus infection in an individual (e.g., a human) is disclosed. In certain embodiments, a compound of any of formula (I), or a pharmaceutically acceptable salt thereof, for use in the prophylactic or therapeutic treatment of an HIV virus infection is disclosed.

In certain embodiments, in the methods of use, the administration is to an individual (e.g., a human) in need of the treatment. In certain embodiments, in the methods of use, the administration is to an individual (e.g., a human) who is at risk of developing AIDS.

Disclosed herein is a compound of formula (I), or a pharmaceutically acceptable salt thereof, for use in therapy. In one embodiment, the compound of formula (I), or a pharmaceutically acceptable salt thereof, is for use in a method of treating an HIV viral infection or the replication of the HIV virus or AIDS or delaying the onset of AIDS in an individual (e.g., a human).

Also disclosed herein is a compound of formula (I), or a pharmaceutically acceptable salt thereof, for use in a method of treating or preventing HIV in an individual in need thereof. In certain embodiments, the individual in need thereof is a human who has been infected with HIV. In certain embodiments, the individual in need thereof is a human who has been infected with HIV but who has not developed AIDS. In certain embodiments, the individual in need thereof is an individual at risk for developing AIDS. In certain embodiments, the individual in need thereof is a human who has been infected with HIV and who has developed AIDS.

Also disclosed herein is a compound of formula (I), or a pharmaceutically acceptable salt thereof, for use in the therapeutic treatment or delaying the onset of AIDS.

Also disclosed herein is a compound of formula (I), or a pharmaceutically acceptable salt thereof, for use in the prophylactic or therapeutic treatment of an HIV infection.

In certain embodiments, a compound of formula (I), or a pharmaceutically acceptable salt thereof can be used as a research tool (e.g. to study the inhibition of HIV reverse transcriptase in a subject or in vitro).

Routes of Administration

One or more compounds disclosed herein which are of the Formula (I) (also referred to herein as the active ingredients) can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the preferred route may vary with, for example, the condition of the recipient. In certain embodiments, the compounds disclosed are orally bioavailable and can be dosed orally.

Dosing Regimen

The compound, such as a compound of Formula (I), may be administered to an individual in accordance with an effective dosing regimen for a desired period of time or duration, such as at least about one month, at least about 2 months, at least about 3 months, at least about 6 months, or at least about 12 months or longer. In one variation, the compound is administered on a daily or intermittent schedule for the duration of the individual's life.

The dosage or dosing frequency of a compound of Formula (I) may be adjusted over the course of the treatment, based on the judgment of the administering physician.

The compound may be administered to an individual (e.g., a human) in an effective amount. In certain embodiments, the compound is administered once daily.

A compound as disclosed herein (e.g., any compound of Formula (I)) may be administered in a dosage amount of the compound of Formula I that is effective. For example, the dosage amount can be from 10 mg to 1000 mg of compound.

Combinations

In certain embodiments, a method for treating or preventing an HIV infection in a human having or at risk of having the infection is disclosed, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents. In one embodiment, a method for treating an HIV infection in a human having or at risk of having the infection is disclosed, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents.

In certain embodiments, the present disclosure relates to a method for treating an HIV infection, comprising administering to a patient in need thereof a therapeutically effective amount of a compound disclosed herein, or a pharmaceutically acceptable salt, thereof, in combination with a therapeutically effective amount of one or more additional therapeutic agents which are suitable for treating an HIV infection.

Also disclosed herein is a compound of formula (I), or a pharmaceutically acceptable salt thereof, and another active ingredient for treating HIV, for use in a method of treating or preventing HIV. In one embodiment, the another active ingredient for treating HIV is selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof.

Also disclosed herein is a compound of formula (I), or a pharmaceutically acceptable salt thereof, for use in a method of treating or preventing HIV, wherein the compound of formula (I) or a pharmaceutically acceptable salt thereof is administered simultaneously, separately or sequentially with another active ingredient for treating HIV. In one embodiment, the another active ingredient for treating HIV is selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof.

A compound as disclosed herein (e.g., any compound of Formula (I)) may be combined with one or more additional therapeutic agents in any dosage amount of the compound of Formula I (e.g., from 10 mg to 1000 mg of compound).

In one embodiment, pharmaceutical compositions comprising a compound disclosed herein, or a pharmaceutically acceptable salt thereof, in combination with one or more (e.g., one, two, three, one or two, or one to three) additional therapeutic agents, and a pharmaceutically acceptable carrier, diluent or excipient are disclosed.

In one embodiment, kits comprising a compound disclosed herein, or a pharmaceutically acceptable salt thereof, in combination with one or more (e.g., one, two, three, one or two, or one to three) additional therapeutic agents are disclosed.

In the above embodiments, the additional therapeutic agent may be an anti-HIV agent. For example, in some embodiments, the additional therapeutic agent is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors (e.g., CCR5 inhibitors, gp41 inhibitors (i.e., fusion inhibitors) and CD4 attachment inhibitors), CXCR4 inhibitors, gp120 inhibitors, G6PD and NADH-oxidase inhibitors, HIV vaccines, HIV maturation inhibitors, latency reversing agents (e.g., histone deacetylase inhibitors, proteasome inhibitors, protein kinase C (PKC) activators, and BRD4 inhibitors), compounds that target the HIV capsid ("capsid inhibitors"; e.g., capsid polymerization inhibitors or capsid disrupting compounds, HIV nucleocapsid p7 (NCp7) inhibitors, HIV p24 capsid protein inhibitors), pharmacokinetic enhancers, immune-based therapies (e.g., Pd-1 modulators, Pd-L1 modulators, toll like receptors modulators, IL-15 agonists), HIV antibodies, bispecific antibodies and "antibody-like" therapeutic proteins (e.g., DARTs®, Duobodies®, Bites®, XmAbs®, TandAbs®, Fab derivatives) including those targeting HIV gp120 or gp41, combination drugs for HIV, HIV p17 matrix protein inhibitors, IL-13 antagonists, Peptidyl-prolyl cis-trans isomerase A modulators, Protein disulfide isomerase inhibitors, Complement C5a receptor antagonists, DNA methyltransferase inhibitor, HIV vif gene modulators, HIV-1 viral infectivity factor inhibitors, TAT protein inhibitors, HIV-1 Nef modulators, Hck tyrosine kinase modulators, mixed lineage kinase-3 (MLK-3) inhibitors, Rev protein inhibitors, Integrin antagonists, Nucleoprotein inhibitors, Splicing factor modulators, COMM domain containing protein 1 modulators, HIV Ribonuclease H inhibitors, Retrocyclin modulators, CDK-9 inhibitors, Dendritic ICAM-3 grabbing nonintegrin 1 inhibitors, HIV GAG protein inhibitors, HIV POL protein inhibitors, Complement Factor H modulators, Ubiquitin ligase inhibitors, Deoxycytidine kinase inhibitors, Cyclin dependent kinase inhibitors Proprotein convertase PC9 stimulators, ATP dependent RNA helicase DDX3X inhibitors, reverse transcriptase priming complex inhibitors, PI3K inhibitors, compounds such as those disclosed in WO 2013/006738 (Gilead Sciences), US 2013/0165489 (University of Pennsylvania), WO 2013/091096A1 (Boehringer Ingelheim), WO 2009/062285 (Boehringer Ingelheim), US20140221380 (Japan Tobacco), US20140221378 (Japan Tobacco), WO 2010/130034 (Boehringer Ingelheim), WO 2013/159064 (Gilead Sciences), WO 2012/145728 (Gilead Sciences), WO2012/003497 (Gilead Sciences), WO2014/100323 (Gilead Sciences), WO2012/145728 (Gilead Sciences), WO2013/159064 (Gilead Sciences) and WO 2012/003498 (Gilead Sciences) and WO 2013/006792 (Pharma Resources), and other drugs for treating HIV, and combinations thereof.

In certain embodiments, the additional therapeutic is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments a compound of Formula (I) is formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, such tablets are suitable for once daily dosing. In certain embodiments, the additional therapeutic agent is selected from one or more of:

(1) Combination drugs selected from the group consisting of ATRIPLA® (efavirenz+tenofovir disoproxil fumarate+emtricitabine), COMPLERA® (EVIPLERA®, rilpivirine+tenofovir disoproxil fumarate+emtricitabine), STRIBILD® (elvitegravir+cobicistat+tenofovir disoproxil fumarate+emtricitabine), dolutegravir+abacavir sulfate+lamivudine, dolutegravir+abacavir sulfate+lamivudine, lamivudine+nevirapine+zidovudine, dolutegravir+rilpivirine, atazanavir sulfate+cobicistat, darunavir+cobicistat, efavirenz+lamivudine+tenofovir disoproxil fumarate, tenofovir alafenamide hemifumarate+emtricitabine+cobicistat+elvitegravir, Vacc-4x+romidepsin, darunavir+tenofovir alafenamide hemifumarate+emtricitabine+cobicistat, APH-0812, raltegravir+lamivudine, KALETRA® (ALUVIA®, lopinavir+ritonavir), atazanavir sulfate+ritonavir, COMBIVIR® (zidovudine+lamivudine, AZT+3TC), EPZICOM® (Livexa®, abacavir sulfate+lamivudine, ABC+3TC), TRIZIVIR® (abacavir sulfate+zidovudine+lamivudine, ABC+AZT+3TC), TRUVADA® (tenofovir disoproxil fumarate+emtricitabine, TDF+FTC), tenofovir+lamivudine and lamivudine+tenofovir disoproxil fumarate;

(2) HIV protease inhibitors selected from the group consisting of amprenavir, atazanavir, fosamprenavir, fosamprenavir calcium, indinavir, indinavir sulfate, lopinavir, ritonavir, nelfinavir, nelfinavir mesylate, saquinavir, saquinavir mesylate, tipranavir, brecanavir, darunavir, DG-17, TMB-657 (PPL-100) and TMC-310911;

(3) HIV non-nucleoside or non-nucleotide inhibitors of reverse transcriptase selected from the group consisting of delavirdine, delavirdine mesylate, nevirapine, etravirine, dapivirine, doravirine, rilpivirine, efavirenz, KM-023, VM-1500, lentinan and AIC-292;

(4) HIV nucleoside or nucleotide inhibitors of reverse transcriptase selected from the group consisting of VIDEX® and VIDEX® EC (didanosine, ddI), zidovudine, emtricitabine, didanosine, stavudine, zalcitabine, lamivudine, censavudine, abacavir, abacavir sulfate, amdoxovir, elvucitabine, alovudine, phosphazid, fozivudine tidoxil, apricitabine, amdoxovir, KP-1461, fosalvudine tidoxil, tenofovir, tenofovir disoproxil, tenofovir disoproxil fumarate, tenofovir disoproxil hemifumarate, tenofovir alafenamide, tenofovir alafenamide hemifumarate, tenofovir alafenamide fumarate, adefovir, adefovir dipivoxil, and festinavir;

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, elvitegravir, dolutegravir andcabotegravir;

(6) HIV non-catalytic site, or allosteric, integrase inhibitors (NCINI) selected from the group consisting of CX-05168, CX-05045 and CX-14442;

(7) HIV gp41 inhibitors selected from the group consisting of enfuvirtide, sifuvirtide and albuvirtide;

(8) HIV entry inhibitors selected from the group consisting of cenicriviroc;

(9) HIV gp120 inhibitors selected from the group consisting of Radha-108 (Receptol) and BMS-663068;

(10) CCR5 inhibitors selected from the group consisting of aplaviroc, vicriviroc, maraviroc, cenicriviroc, PRO-140, Adaptavir (RAP-101), TBR-220 (TAK-220) and vMIP (Haimipu);

(11) CD4 attachment inhibitors selected from the group consisting of ibalizumab;

(12) CXCR4 inhibitors selected from the group consisting of plerixafor, ALT-1188, vMIP and Haimipu;

(13) Pharmacokinetic enhancers selected from the group consisting of cobicistat and ritonavir;

(14) Immune-based therapies selected from the group consisting of dermaVir, interleukin-7, lexgenleucel-T (VRX-496), plaquenil (hydroxychloroquine), proleukin (aldesleukin, IL-2), interferon alfa, interferon alfa-2b, interferon alfa-n3, pegylated interferon alfa, interferon gamma, hydroxyurea, mycophenolate mofetil (MPA) and its ester derivative mycophenolate mofetil (MMF), WF-10, ribavirin, IL-2, IL-2 XL, IL-12, polymer polyethyleneimine (PEI), Gepon, VGV-1, MOR-22, BMS-936559, toll-like receptors modulators (tlr1, tlr2, tlr3, tlr4, tlr5, tlr6, tlr7, tlr8, tlr9, tlr10, tlr11, tlr12 and tlr13), rintatolimod and IR-103;

(15) HIV vaccines selected from the group consisting of peptide vaccines, recombinant subunit protein vaccines, live vector vaccines, DNA vaccines, virus-like particle vaccines (pseudovirion vaccine), CD4-derived peptide vaccines, vaccine combinations, rgp120 (AIDSVAX), ALVAC HIV (vCP1521)/AIDSVAX B/E (gp120) (RV144), Remune, ITV-1, Contre Vir, Ad5-ENVA-48, DCVax-001, (CDX-2401), PEP-6409, Vacc-4x, Vacc-05, VAC-3S, multiclade DNA recombinant adenovirus-5 (rAd5), Pennvax-G, VRC-HIV MAB060-00-AB, AVX-101, Tat Oyi vaccine, AVX-201, HIV-LAMP-vax, Ad35, Ad35-GRIN, NAcGM3/VSSP ISA-51, poly-ICLC adjuvanted vaccines, TatImmune, GTU-multiHIV (FIT-06), AGS-004, gp140[delta]V2.TV1+MF-59, rVSVIN HIV-1 gag vaccine, SeV-Gag vaccine, AT-20, DNK-4, Ad35-GRIN/ENV, TBC-M4, HIVAX, HIVAX-2, NYVAC-HIV-PT1, NYVAC-HIV-PT4, DNA-HIV-PT123, Vichrepol, rAAV1-PG9DP, GOVX-B11, GOVX-B21, ThV-01, TUTI-16, VGX-3300, TVI-HIV-1, Ad-4 (Ad4-env Clade C+Ad4-mGag), EN41-UGR7C, EN41-FPA2, PreVaxTat, TL-01, SAV-001, AE-H, MYM-V101, CombiHIVvac, ADVAX, MYM-V201, MVA-CMDR and DNA-Ad5 gag/pol/nef/nev (HVTN505);

(16) HIV antibodies, bispecific antibodies and "antibody-like" therapeutic proteins (such as DARTs®, Duobodies®, Bites®, XmAbs®, TandAbs®, Fab derivatives) including BMS-936559, TMB-360 and those targeting HIV gp120 or gp41 selected from the group consisting of bavituximab, UB-421, C2F5, C2G12, C4E10, C2F5+C2G12+C4E10, 3-BNC-117, KD-247, PGT145, PGT121, MDX010 (ipilimumab), VRC01, A32, 7B2, 10E8 and VRC07;

(17) latency reversing agents selected from the group consisting of Histone deacetylase inhibitors such as Romidepsin, vorinostat, panobinostat; Proteasome inhibitors such as Velcade; protein kinase C (PKC) activators such as Indolactam, Prostratin, Ingenol B and DAG-lactones, Ionomycin, GSK-343, PMA, SAHA, BRD4 inhibitors, IL-15, JQ1, disulfram, and amphotericin B;

(18) HIV nucleocapsid p7 (NCp7) inhibitors selected from the group consisting of azodicarbonamide;

(19) HIV maturation inhibitors selected from the group consisting of BMS-955176 and GSK-2838232;

(20) PI3K inhibitors selected from the group consisting of idelalisib, AZD-8186, buparlisib, CLR-457, pictilisib, neratinib, rigosertib, rigosertib sodium, EN-3342, TGR-1202, alpelisib, duvelisib, UCB-5857, taselisib, XL-765, gedatolisib, VS-5584, copanlisib, CAI orotate, perifosine, RG-7666, GSK-2636771, DS-7423, panulisib, GSK-2269557, GSK-2126458, CUDC-907, PQR-309, INCB-040093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301 and CLR-1401;

(21) the compounds disclosed in WO 2004/096286 (Gilead Sciences), WO 2006/110157 (Gilead Sciences), WO 2006/015261 (Gilead Sciences), WO 2013/006738 (Gilead Sciences), US 2013/0165489 (University of Pennsylvania), US20140221380 (Japan Tobacco), US20140221378 (Japan Tobacco), WO 2013/006792 (Pharma Resources), WO 2009/062285 (Boehringer Ingelheim), WO 2010/130034 (Boehringer Ingelheim), WO 2013/091096A1 (Boehringer Ingelheim), WO 2013/159064 (Gilead Sciences), WO 2012/145728 (Gilead Sciences), WO2012/003497 (Gilead Sciences), WO2014/100323 (Gilead Sciences), WO2012/145728 (Gilead Sciences), WO2013/159064 (Gilead Sciences) and WO 2012/003498 (Gilead Sciences); and

(22) other drugs for treating HIV selected from the group consisting of TR-452, MK-8591, REP 9, CYT-107, alisporivir, NOV-205, IND-02, metenkefalin, PGN-007, Acemannan, Gamimune, SCY-635, Prolastin, 1,5-dicaffeoylquinic acid, BIT-225, RPI-MN, VSSP, Hlviral, IMO-3100, SB-728-T, RPI-MN, VIR-576, HGTV-43, MK-1376, rHIV7-sh1-TAR-CCR5RZ, MazF gene therapy, BlockAide and PA-1050040 (PA-040).

In certain embodiments, a compound disclosed herein, or a pharmaceutically acceptable salt thereof, is combined with one, two, three, four or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents. In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In a further embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase.

In a particular embodiment, a compound disclosed herein, or a pharmaceutically acceptable salt thereof, is combined with one, two, three, four or more additional therapeutic agents selected from raltegravir, Truvada® (tenofovir disoproxil fumarate+emtricitabine, TDF+FTC), maraviroc, enfuvirtide, Epzicom® (Livexa®, abacavir sulfate+lamivudine, ABC+3TC), Trizivir® (abacavir sulfate+zidovudine+lamivudine, ABC+AZT+3TC), adefovir, adefovir dipivoxil, Stribild® (elvitegravir+cobicistat+tenofovir disoproxil fumarate+emtricitabine), rilpivirine, rilpivirine hydrochloride, Complera® (Eviplera®, rilpivirine+tenofovir disoproxil fumarate+emtricitabine), Cobicistat, Atripla® (efavirenz+tenofovir disoproxil fumarate+emtricitabine), atazanavir, atazanavirsulfate, dolutegravir, elvitegravir, Aluvia® (Kaletra®, lopinavir+ritonavir), ritonavir, emtricitabine, atazanavir_sulfate+ritonavir, darunavir, lamivudine, Prolastin, fosamprenavir, fosamprenavir calcium, efavirenz, Combivir® (zidovudine+lamivudine, AZT+3TC), etravirine, nelfinavir, nelfinavir mesylate, interferon, didanosine, stavudine, indinavir, indinavir sulfate, tenofovir+lamivudine, zidovudine, nevirapine, saquinavir, saquinavir mesylate, aldesleukin, zalcitabine, tipranavir, amprenavir, delavirdine, delavirdine mesylate, Radha-108 (Receptol), Hlviral, lamivudine+tenofovir disoproxil fumarate, efavirenz+lamivudine+tenofovir disoproxil fumarate, phosphazid, lamivudine+nevirapine+zidovudine, abacavir, abacavir sulfate, tenofovir, tenofovir disoproxil, tenofovir disoproxil fumarate, tenofovir alafenamide and tenofovir alafenamide hemifumarate.

In a particular embodiment, a compound disclosed herein, or a pharmaceutically acceptable salt thereof, is combined with abacavir sulfate, tenofovir, tenofovir disoproxil, tenofovir disoproxil fumarate, tenofovir disoproxil hemifumarate, tenofovir alafenamide or tenofovir alafenamide hemifumarate.

In a particular embodiment, a compound disclosed herein, or a pharmaceutically acceptable salt thereof, is combined with tenofovir, tenofovir disoproxil, tenofovir disoproxil fumarate, tenofovir alafenamide, or tenofovir alafenamide hemifumarate.

In a particular embodiment, a compound disclosed herein, or a pharmaceutically acceptable salt thereof, is combined with a first additional therapeutic agent selected from the group consisting of: abacavir sulfate, tenofovir, tenofovir disoproxil, tenofovir disoproxil fumarate, tenofovir alafenamide, and tenofovir alafenamide hemifumarate and a second additional therapeutic agent selected from the group consisting of emtricitabine and lamivudine.

In a particular embodiment, a compound disclosed herein, or a pharmaceutically acceptable salt thereof, is combined with a first additional therapeutic agent selected from the group consisting of: tenofovir, tenofovir disoproxil, tenofovir disoproxil fumarate, tenofovir alafenamide, and tenofovir alafenamide hemifumarate and a second additional therapeutic agent, wherein the second additional therapeutic agent is emtricitabine.

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide and 200 mg emtricitabine. In certain embodiments, a compound disclosed herein, or a pharmaceutically acceptable salt thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide and 200 mg emtricitabine. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide and 200 mg emtricitabine. In certain embodiments; a compound disclosed herein, or a pharmaceutically acceptable salt thereof, is combined with 25 mg tenofovir alafenamide fumarate, tenofovir alafenamide hemifumarate, or tenofovir alafenamide and 200 mg emtricitabine. A compound as disclosed herein (e.g., a compound of formula (I)) may be combined with the agents disclosed herein in any dosage amount of the compound (e.g., from 10 mg to 500 mg of compound) the same as if each combination of dosages were specifically and individually listed.

In certain embodiments, a compound disclosed herein, or a pharmaceutically acceptable salt thereof, is combined with 200-400 mg tenofovir disoproxil fumarate, tenofovir disoproxil hemifumarate, or tenofovir disoproxil and 200 mg emtricitabine. In certain embodiments, a compound disclosed herein, or a pharmaceutically acceptable salt thereof, is combined with 200-250; 200-300; 200-350; 250-350; 250-400; 350-400; 300-400; or 250-400 mg tenofovir disoproxil fumarate, tenofovir disoproxil hemifumarate, or tenofovir disoproxil and 200 mg emtricitabine. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil and 200 mg emtricitabine. A compound as disclosed herein (e.g., a compound of formula (I)) may be combined with the agents disclosed herein in any dosage amount of the compound (e.g., from 10 mg to 500 mg of compound) the same as if each combination of dosages were specifically and individually listed.

In certain embodiments, when a compound disclosed herein is combined with one or more additional therapeutic agents as described above, the components of the composition are administered as a simultaneous or sequential regimen. When administered sequentially, the combination may be administered in two or more administrations.

In certain embodiments, a compound disclosed herein is combined with one or more additional therapeutic agents in a unitary dosage form for simultaneous administration to a patient, for example as a solid dosage form for oral administration.

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and one or more additional therapeutic agents are both present in the body of the patient.

Co-administration includes administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

In certain embodiments, a method for treating or preventing an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents. In one embodiment, a method for treating an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents.

In one embodiment, pharmaceutical compositions comprising a compound disclosed herein, or a pharmaceutically acceptable salt thereof, in combination with one or more (e.g., one, two, three, one or two, or one to three) additional therapeutic agents, and a pharmaceutically acceptable carrier, diluent, or excipient are provided.

In certain embodiments, the present disclosure provides a method for treating an HIV infection, comprising administering to a patient in need thereof a therapeutically effective amount of a compound disclosed herein, or a pharmaceutically acceptable salt thereof, in combination with a therapeutically effective amount of one or more additional therapeutic agents which are suitable for treating an HIV infection.

In certain embodiments, a compound disclosed herein, or a pharmaceutically acceptable salt thereof, is combined with one, two, three, four, or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four, or more additional therapeutic agents can be different therapeutic agents selected from the same class of therapeutic agents, and/or they can be selected from different classes of therapeutic agents.

Administration of HIV Combination Therapy

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and the one or more additional therapeutic agents are both present in the body of the patient. When administered sequentially, the combination may be administered in two or more administrations.

Co-administration includes administration of unit dosages of the compounds disclosed herein before or after administration of unit dosages of one or more additional therapeutic agents. For example, the compound disclosed herein may be administered within seconds, minutes, or hours of the administration of the one or more additional therapeutic agents. In some embodiments, a unit dose of a compound disclosed herein is administered first, followed within seconds or minutes by administration of a unit dose of one or more additional therapeutic agents. Alternatively, a unit dose of one or more additional therapeutic agents is administered first, followed by administration of a unit dose of a compound disclosed herein within seconds or minutes. In other embodiments, a unit dose of a compound disclosed herein is administered first, followed, after a period of hours (e.g., 1-12 hours), by administration of a unit dose of one or more additional therapeutic agents. In yet other embodiments, a unit dose of one or more additional therapeutic agents is administered first, followed, after a period of hours (e.g., 1-12 hours), by administration of a unit dose of a compound disclosed herein.

In certain embodiments, a compound disclosed herein is combined with one or more additional therapeutic agents in a unitary dosage form for simultaneous administration to a patient, for example as a solid dosage form for oral administration.

In certain embodiments, a compound of Formula (I) is formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, such tablets are suitable for once daily dosing.

HIV Combination Therapy

In the above embodiments, the additional therapeutic agent may be an anti-HIV agent. For example, in some embodiments, the additional therapeutic agent is selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

HIV Combination Drugs

Examples of combination drugs include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide, emtricitabine, and rilpivirine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; lopinavir, ritonavir, zidovudine and lamivudine; Vacc-4x and romidepsin; and APH-0812.

Other HIV Drugs

Examples of other drugs for treating HIV include acemannan, alisporivir, BanLec, deferiprone, Gamimune, metenkefalin, naltrexone, Prolastin, REP 9, RPI-MN, VSSP, Hlviral, SB-728-T, 1,5-dicaffeoylquinic acid, rHIV7-sh1-TAR-CCR5RZ, AAV-eCD4-Ig gene therapy, MazF gene therapy, BlockAide, ABX-464, AG-1105, BIT-225, CYT-107, HGTV-43, HS-10234, IMO-3100, IND-02, MK-1376, MK-8507, MK-8591, NOV-205, PA-1050040 (PA-040), PGC-007, SCY-635, TR-452, TEV-90110, TEV-90112, TEV-90111, TEV-90113, RN-18, Immuglo, and VIR-576.

HIV Protease Inhibitors

Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, and TMC-310911.

HIV Reverse Transcriptase Inhibitors

Examples of HIV non-nucleoside or non-nucleotide inhibitors of reverse transcriptase include dapivirine, delavirdine, delavirdine mesylate, doravirine, efavirenz, etravirine, lentinan, nevirapine, rilpivirine, AIC-292, KM-023, and VM-1500.

Examples of HIV nucleoside or nucleotide inhibitors of reverse transcriptase include adefovir, adefovir dipivoxil, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, fozivudine tidoxil, lamivudine, phosphazid, stavudine, zalcitabine, zidovudine, and KP-1461.

HIV Integrase Inhibitors

Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, and cabotegravir.

Examples of HIV non-catalytic site, or allosteric, integrase inhibitors (NCINI) include CX-05045, CX-05168, T-169, and CX-14442.

HIV Entry Inhibitors

Examples of HIV entry (fusion) inhibitors include cenicriviroc, CCR5 inhibitors, gp41 inhibitors, CD4 attachment inhibitors, gp120 inhibitors, and CXCR4 inhibitors.

Examples of CCR5 inhibitors include aplaviroc, vicriviroc, maraviroc, cenicriviroc, PRO-140, adaptavir (RAP-101), nifeviroc (TD-0232), TD-0680, and vMIP (Haimipu).

Examples of gp41 inhibitors include albuvirtide, enfuvirtide, and sifuvirtide.

Examples of CD4 attachment inhibitors include ibalizumab.

Examples of gp120 inhibitors include Radha-108 (receptol) and BMS-663068

Examples of CXCR4 inhibitors include plerixafor, and vMIP (Haimipu).

HIV Maturation Inhibitors

Examples of HIV maturation inhibitors include BMS-955176 and GSK-2838232.

Latency Reversing Agents

Examples of latency reversing agents include histone deacetylase (HDAC) inhibitors, proteasome inhibitors such as velcade, protein kinase C (PKC) activators, BET-bromodomain 4 (BRD4) inhibitors, ionomycin, PMA, SAHA (suberanilohydroxamic acid, or suberoyl, anilide, and hydroxamic acid), IL-15, JQ1, disulfram, amphotericin B, and GSK-343.

Examples of HDAC inhibitors include romidepsin, vorinostat, and panobinostat.

Examples of PKC activators include indolactam, prostratin, ingenol B, and DAG-lactones.

Capsid Inhibitors

Examples of capsid inhibitors include capsid polymerization inhibitors or capsid disrupting compounds, HIV nucleocapsid p7 (NCp7) inhibitors such as azodicarbonamide, and HIV p24 capsid protein inhibitors.

Immune-Based Therapies

Examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 agonists; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; polymer polyethyleneimine (PEI); gepon; rintatolimod; IL-12; WF-10; VGV-1; MOR-22; BMS-936559; GS-9620; and IR-103.

Phosphatidylinositol 3-Kinase (PI3K) Inhibitors

Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

HIV Antibodies, Bispecific Antibodies, and "Antibody-Like" Therapeutic Proteins

Examples of HIV antibodies, bispecific antibodies, and "antibody-like" therapeutic proteins include DARTs®, DUOBODIES®, BITES®, XmAbs®, TandAbs®, Fab derivatives, BMS-936559, TMB-360, and those targeting HIV gp120 or gp41.

Examples of those targeting HIV gp120 or gp41 include bavituximab, UB-421, C2F5, C2G12, C4E10, C2F5+C2G12+C4E10, 3-BNC-117, PGT145, PGT121, MDX010 (ipilimumab), VRC01, A32, 7B2, 10E8, VRC-07-523, MGD-014 and VRC07.

Pharmacokinetic Enhancers

Examples of pharmacokinetic enhancers include cobicistat and ritonavir.

Additional Therapeutic Agents

Examples of additional therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489. (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences); WO 2013/091096 (Boehringer Ingelheim); and US 20100143301 (Gilead Sciences).

HIV Vaccines

Examples of HIV vaccines include peptide vaccines, recombinant subunit protein vaccines, live vector vaccines, DNA vaccines, CD4-derived peptide vaccines, vaccine combinations, rgp120 (AIDSVAX), ALVAC HIV (vCP1521)/AIDSVAX B/E (gp120) (RV144), monomeric gp120 HIV-1 subtype C vaccine, Remune, ITV-1, Contre Vir, Ad5-ENVA-48, DCVax-001 (CDX-2401), Vacc-4x, Vacc-05, VAC-3S, multiclade DNA recombinant adenovirus-5 (rAd5), Pennvax-G, Pennvax-GP, VRC-HIV MAB060-00-AB, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multiHIV (FIT-06), gp140 [delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, TVI-HIV-1, Ad-4 (Ad4-env Clade C+Ad4-mGag), EN41-UGR7C, EN41-FPA2, PreVaxTat, AE-H, MYM-V101, CombiHIVvac, ADVAX, MYM-V201, MVA-CMDR, DNA-Ad5 gag/pol/nef/nev (HVTN505), MVATG-17401, ETV-01, CDX-1401, rcAD26.MOS1.HIV-Env, Ad26.Mod.HIV vaccine, AGS-004, AVX-101, AVX-201, PEP-6409, SAV-001, ThV-01, TL-01, TUTI-16, VGX-3300, IHV-001, and virus-like particle vaccines such as pseudovirion vaccine.

HIV Combination Therapy

In a particular embodiment, a compound disclosed herein, or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); Hlviral; lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase.

In a particular embodiment, a compound disclosed herein, or a pharmaceutically acceptable salt thereof, is combined with abacavir sulfate, tenofovir, tenofovir disoproxil, tenofovir disoproxil fumarate, tenofovir disoproxil hemifumarate, tenofovir alafenamide, or tenofovir alafenamide hemifumarate.

In a particular embodiment, a compound disclosed herein, or a pharmaceutically acceptable salt thereof, is combined with tenofovir, tenofovir disoproxil, tenofovir disoproxil fumarate, tenofovir alafenamide, or tenofovir alafenamide hemifumarate.

In a particular embodiment, a compound disclosed herein, or a pharmaceutically acceptable salt thereof, is combined with a first additional therapeutic agent selected from the group consisting of abacavir sulfate, tenofovir, tenofovir disoproxil, tenofovir disoproxil fumarate, tenofovir alafenamide, and tenofovir alafenamide hemifumarate, and a second additional therapeutic agent selected from the group consisting of emtricitabine and lamivudine.

In a particular embodiment, a compound disclosed herein, or a pharmaceutically acceptable salt thereof, is combined with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine.

A compound as disclosed herein (e.g., any compound of Formula (I)) may be combined with one or more additional therapeutic agents in any dosage amount of the compound of Formula (I) (e.g., from 50 mg to 1000 mg of compound).

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 5-10, 5-15, 5-20, 5-25, 25-30, 20-30, 15-30, or 10-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide, and 200 mg emtricitabine. A compound as disclosed herein (e.g., a compound of formula (I)), may be combined with the agents provided herein in any dosage amount of the compound (e.g., from 50 mg to 500 mg of compound) the same as if each combination of dosages were specifically and individually listed.

In certain embodiments, a compound disclosed herein, or a pharmaceutically acceptable salt thereof, is combined with 200-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 200-250, 200-300, 200-350, 250-350, 250-400, 350-400, 300-400, or 250-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil, and 200 mg emtricitabine. A compound as disclosed herein (e.g., a compound of formula (I)) may be combined with the agents provided herein in any dosage amount of the compound (e.g., from 50 mg to 500 mg of compound) the same as if each combination of dosages were specifically and individually listed.

In one embodiment, kits comprising a compound disclosed herein, or a pharmaceutically acceptable salt thereof, in combination with one or more (e.g., one, two, three, one or two, or one to three) additional therapeutic agents are provided.

Kits and Articles of Manufacture

The present disclosure relates to a kit comprising a compound of formula (I), or a pharmaceutically acceptable salt thereof. The kit may further comprise instructions for use, e.g., for use in inhibiting an HIV reverse transcriptase, such as for use in treating an HIV infection or AIDS or as a research tool. The instructions for use are generally written instructions, although electronic storage media (e.g., magnetic diskette or optical disk) containing instructions are also acceptable.

The present disclosure also relates to a pharmaceutical kit comprising one or more containers comprising a compound of any of formula (I), or a pharmaceutically acceptable salt thereof. Optionally associated with such container(s) can be a notice in the form prescribed by a governmental agency regulating the manufacture, use or sale of pharmaceuticals, which notice reflects approval by the agency for the manufacture, use or sale for human administration. Each component (if there is more than one component) can be packaged in separate containers or some components can be combined in one container where cross-reactivity and shelf life permit. The kits may be in unit dosage forms, bulk packages (e.g., multi-dose packages) or sub-unit doses. Kits may also include multiple unit doses of the compounds and instructions for use and be packaged in quantities sufficient for storage and use in pharmacies (e.g., hospital pharmacies and compounding pharmacies).

Also disclosed are articles of manufacture comprising a unit dosage of a compound of any of formula (I), or a pharmaceutically acceptable salt thereof, in suitable packaging for use in the methods described herein. Suitable packaging is known in the art and includes, for example, vials, vessels, ampules, bottles, jars, flexible packaging and the like. An article of manufacture may further be sterilized and/or sealed.

The present disclosure is also directed to processes and intermediates useful for preparing the subject compounds or pharmaceutically acceptable salts thereof.

Many general references providing commonly known chemical synthetic schemes and conditions useful for synthesizing the disclosed compounds are available (see, e.g., Smith, March's Advanced Organic Chemistry: Reactions, Mechanisms, and Structure, 7$^{th}$ edition, Wiley-Interscience, 2013.)

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd ed., ed. L. R. Snyder and J. J. Kirkland, John Wiley and Sons, 1979; and Thin Layer Chromatography, E. Stahl (ed.), Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4$^{th}$ ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used. Unless otherwise specified, the variables are as defined above in reference to formula (I).

Representative syntheses of compounds of the present disclosure are described in schemes below, and the particular examples that follow.

The embodiments are also directed to processes and intermediates useful for preparing the subject compounds or pharmaceutically acceptable salts thereof.

Many general references providing commonly known chemical synthetic schemes and conditions useful for synthesizing the disclosed compounds are available (see, e.g., Smith, March's Advanced Organic Chemistry: Reactions, Mechanisms, and Structure, 7$^{th}$ edition, Wiley-Interscience, 2013.). Angew. Chem. Int. Ed. 2014, 53, 2-21, which is herein incorporated by reference in its entirety, provides a review of sulfur (VI) fluoride exchange, which can also be useful in the synthetic schemes.

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd ed., ed. L. R. Snyder and J. J. Kirkland, John Wiley and Sons, 1979; and Thin Layer Chromatography, E. Stahl (ed.), Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4$^{th}$ ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes may be run at a temperature from about 0° C. to the reflux temperature of the organic solvent used. Unless otherwise specified, the variables are as defined above in reference to formula (I).

Representative syntheses of compounds of the present disclosure are described in schemes below, and the particular examples that follow.

Scheme 1 shows a representative synthesis of the compounds of the embodiments. The methodology is compatible with a wide variety of functionalities.

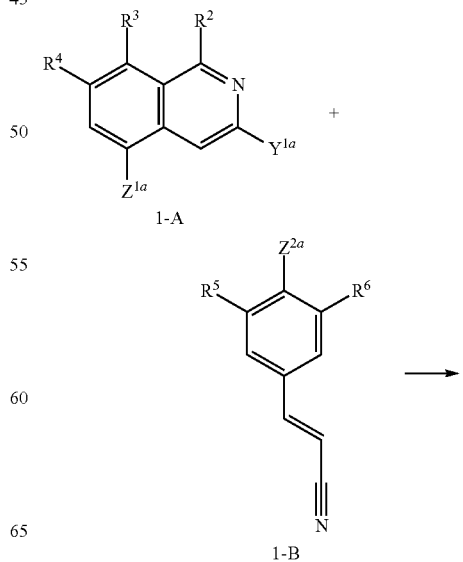

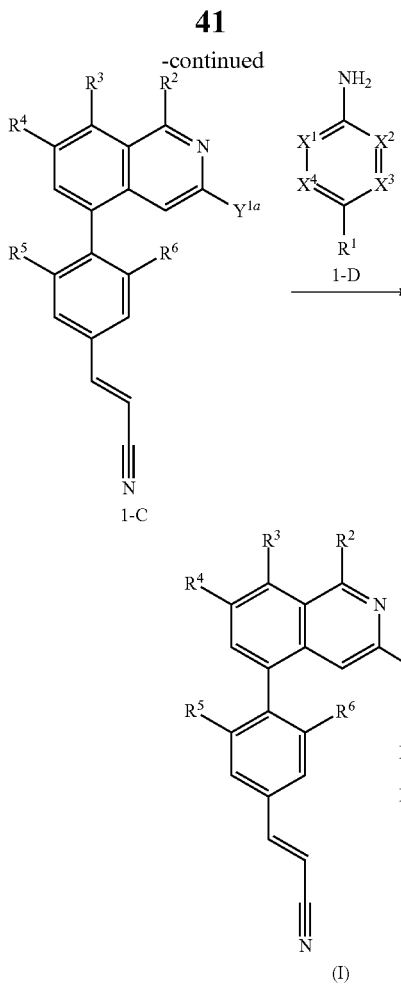

1-C

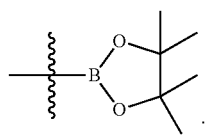 [SMILES: *B1OC(C)(C)C(C)(C)O1]

(I)

In Scheme 1, $R^1$, $R^2$, $R^3$, $R^4$, $R^5$, $R^6$, $X^1$, $X^2$, $X^3$, and $X^4$ are as defined herein. Also in Scheme 1, as discussed below, $Y^{1a}$, $Z^{1a}$, and $Z^{2a}$ are precursor moieties to forming the proper bonds and moieties in formula (I). Starting materials may be obtained from commercial sources or via well-established synthetic procedures. The synthesis of formula 1-B is discussed below in Scheme 2.

With reference to Scheme 1, a coupling reaction between formula 1-A and 1-B occurs to produce formula 1-C. In certain instances, a palladium-catalyzed reaction between an aryl halide and an organoboron compound (e.g., Suzuki coupling reaction) can be used. With a Suzuki coupling reaction, $Z^{1a}$ in formula 1-A can be a halide, such as iodo or bromo and $Z^{2a}$ in formula 1-B can be a boronic acid or boronic acid ester. In certain instances, $Z^{2a}$ is

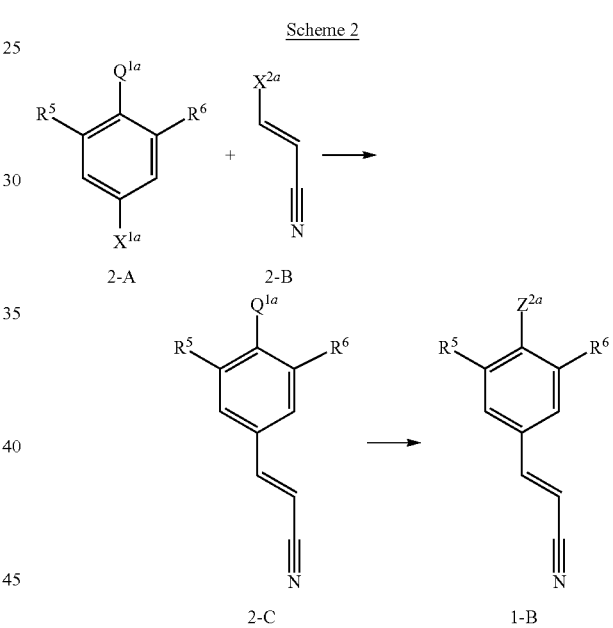

In certain instances, the coupling step includes a palladium catalyst, such as 1,1'-bis(di-tert-butylphosphino)ferrocene palladium dichloride or 1,1'-bis(diphenylphosphino)ferrocene palladium dichloride.

With continued reference to Scheme 1, as an alternative coupling reaction between formula 1-A and 1-B, a palladium-catalyzed reaction between an organotin compound and an aryl halide (e.g., Stille coupling reaction) can be used to produce a compound of formula (I). With the Stille reaction, $Z^{1a}$ in formula 1-A can be an organotin moiety (—$SnR_4$, where R is an alkyl group) and $Z^{2a}$ in formula 1-B can be a halide, such as iodo or bromo. In certain instances, the coupling step includes a palladium catalyst, such as bis(tri-tert-butylphosphine)palladium(0).

With continued reference to Scheme 1, a coupling reaction between formula 1-C and 1-D occurs to produce a compound of formula (I). The amino group of formula 1-D reacts with formula 1-C to displace $Y^{1a}$, which is a leaving group, such as halogen, triflate, mesylate, and tosylate. In certain instances, $Y^{1a}$ is halogen, such as iodo, bromo, or chloro. In certain instances, the coupling step includes a palladium catalyst, such as palladium (II) acetate in a combination with (9,9-dimethyl-9H-xanthene-4,5-diyl)bis(diphenylphosphine).

Scheme 2 shows a representative synthesis of formula 1-B. The methodology is compatible with a wide variety of functionalities.

In Scheme 2, $R^5$ and $R^6$ are as defined herein. Also in Scheme 2, as discussed below, $Q^{1a}$, $X^{1a}$, and $X^{2a}$ are precursor moieties to forming the proper bonds and moieties in formula 1-B. Starting materials may be obtained from commercial sources or via well-established synthetic procedures.

In Scheme 2, a coupling reaction between formula 2-A and 2-B occurs to produce formula 2-C. In certain instances, a palladium-catalyzed reaction between an aryl halide and an alkene compound (e.g., Heck coupling reaction) can be used. With a Heck coupling reaction, $X^{1a}$ in formula 2-A can be a halide, such as iodo or bromo and $X^{2a}$ in formula 2-B can be hydrogen. The Heck coupling reaction can be carried out in the presence of a palladium catalyst, such as palladium(II) acetate in a combination with tri(o-tolyl)phosphine.

With continued reference to Scheme 2, $Q^{1a}$ in formula 2-A and 2-C is a precursor moiety to a boronic acid in formula 1-B, wherein $Z^{2a}$ is a boronic acid or boronic acid ester. A borylation reaction of formula 2-C occurs to produce a compound of formula 1-B. In certain instances, a cross-coupling reaction of 4,4,4',4',5,5,5',5'-octamethyl-2,2'-bi(1,3,2-dioxaborolane) with an aryl halide (e.g., Miyaura borylation reaction) can be used. With a Miyaura borylation reaction, $Q^{1a}$ in formula 2-C can be a halide, such as iodo, or bromo. In certain instances, Formula 2-C can react with 4,4,4',4',5,5,5',5'-octamethyl-2,2'-bi(1,3,2-dioxaborolane) to provide for formula 1-B, in which $Z^{2a}$ is

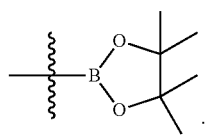 [SMILES: *B1OC(C)(C)C(C)(C)O1]

In certain instances, the borylation step includes a palladium catalyst, such as palladium(II) acetate in a combination with dicyclohexyl(2',6'-dimethoxy-[1,1'-biphenyl]-2-yl)phosphine. Other borylation reactions can be used.

Accordingly, and as described in more detail herein, the present disclosure relates to a process of preparing a compound of the present disclosure, the process involving: reacting a compound of formula:

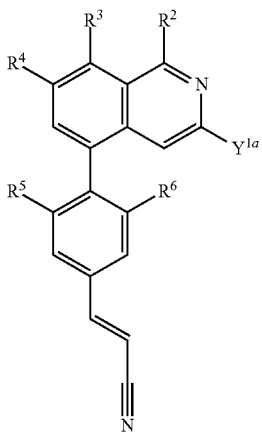

(1-C)

with a compound of formula:

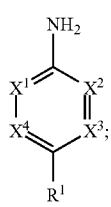

(1-D)

thereby producing a compound of formula

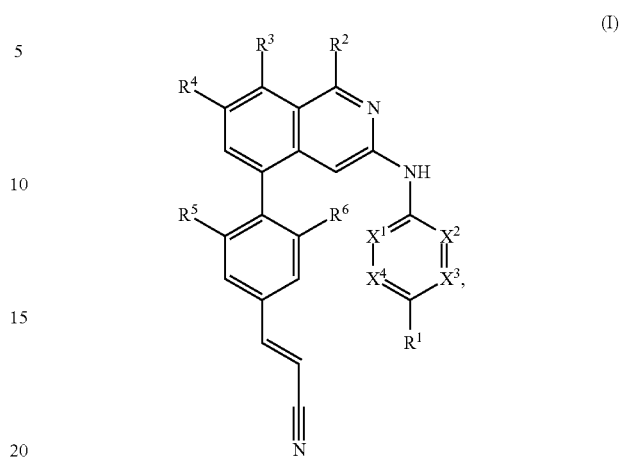

(I)

wherein $R^1$, $R^2$, $R^3$, $R^4$, $R^5$, $R^6$, $X^1$, $X^2$, $X^3$, $X^4$, and $Y^{1a}$ are as defined herein.

In certain instances, the above processes further involve the step of forming a salt of a compound of the present disclosure. Embodiments are directed to the other processes described herein; and to the product prepared by any of the processes described herein.

Except as otherwise noted, the methods and techniques of the present disclosure are generally performed according to conventional methods well known in the art and as described in various general and more specific references that are cited and discussed throughout the present specification. See, e.g., Loudon, Organic Chemistry, 5$^{th}$ edition, New York: Oxford University Press, 2009; Smith, March's Advanced Organic Chemistry: Reactions, Mechanisms, and Structure, 7$^{th}$ edition, Wiley-Interscience, 2013.

LIST OF ABBREVIATIONS AND ACRONYMS

Abbreviation—Meaning
Ac—Acetyl
B$_2$pin$_2$—4,4,4',4',5,5,5',5'-Octamethyl-2,2'-bi(1,3,2-dioxaborolane)
bs—Broad singlet
° C.—Degree Celsius
d—Doublet
DCM—Dichloromethane
dd—Doublet of doublet
DIPEA—N,N-Diisopropylethylamine
DMF—N,N-Dimethylformamide
DMSO—Dimethylsulfoxide
dppf—1,1'-Bis(diphenylphosphino)ferrocene
dtbpf—1,1'-Bis(di-tert-butylphosphino)ferrocene
EC$_{50}$—Half maximal effective concentration.
Equiv/eq—Equivalents
Et—Ethyl
EtOH—Ethanol
g—Grams
HPLC—High-performance liquid chromatography
hrs/h—Hours
Hz—Hertz
J—Coupling constant
LCMS—Liquid chromatography-mass spectrometry
M—Molar
m—Multiplet
m/z—mass-to-charge ratio
M+—Mass peak Me—Methyl
mg—Milligram
MHz—Megahertz
min—Minute
mL—Milliliter
mM—Millimolar
mm—Millimeter
mmol—Millimole
mol—Mole
MS—Mass spectrometry
MW—Microwave
nM—Nanomolar
NMP—N-Methyl-2-pyrrolidone
NMR—Nuclear magnetic resonance
P(oTol)$_3$—Tri(o-tolyl)phosphine
q—Quartet
quant—Quantitative
Rf—Retention factor
RT/rt/r.t.—Room temperature
s—Singlet
sat.—Saturated
SPhos—Dicyclohexyl(2',6'-dimethoxy-[1,1'-biphenyl]-2-yl)phosphine
t—Triplet
TFA—Trifluoroacetic acid
TMS—Trimethylsilyl
Tr/tr—Retention time
UV—Ultraviolet
wt.—Weight
Xantphos—(9,9-Dimethyl-9H-xanthene-4,5-diyl)bis(diphenylphosphine)
δ—Chemical shift
μL—Microliter
μM—Micromolar
μmol—Micromole The following examples are merely illustrative, and not intended to limit this disclosure in any way. Unless otherwise stated, preparative HPLC was performed on a Gilson HPLC system, using a 21.2×250 mm 10 micron C18 Phenomenex Gemini semi-preparative column and acetonitrile/water mobile phase with 0.1% trifluoroacetic acid at a flow rate of 20 mL/min.

Chemical names for certain compounds were generated using ChemBioDraw 12.0 software.

The following methods were used for the purification and characterization of certain compounds described in the following Examples.

LCMS method 1—Gemini 5 u C18 110 Å, 50×4.60 mm 5 micron column; Acetonitrile with 0.1% acetic acid, Water with 0.1% acetic acid; Gradient: 0 min-3.5 min 5-100% ACN; flow rate 2 mL/min.

LCMS method 2—Kinetex 2.6μ C18 100 A, 50×3.00 mm column; Acetonitrile with 0.1% formic acid, Water with 0.1% formic acid; Gradient: 0 min-1.5 min 2-100% ACN, 1.5 min-2.8 min 100% ACN, 2.8 min-2.85 min 100%-2% ACN, 2.85 min-3 min 2% ACN; flow rate 1.8 mL/min.

LCMS method 3—Kinetex 2.6μ C18 100 A, 50×3.00 mm column; Acetonitrile with 0.1% formic acid, Water with 0.1% formic acid; Gradient: 0 min-1.4 min 2-100% ACN, 1.4 min-1.8 min 100% ACN, 1.8 min-1.85 min 100%-2% ACN, 1.85 min-2 min 2% ACN; flow rate 1.8 mL/min.

EXAMPLE 1

(E)-2-((1-Amino-5-(4-(2-cyanovinyl)-2,6-dimethylphenyl)isoquinolin-3-yl)amino)pyrimidine-5-carbonitrile—Compound 1

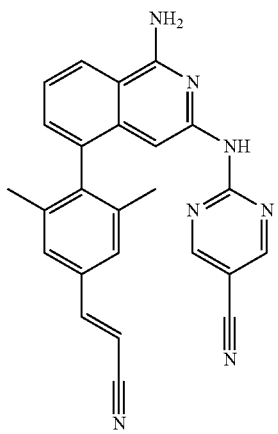 [SMILES: Cc1cc(/C=C/C#N)cc(C)c1-c1cccc2c(N)nc(Nc3ncc(C#N)cn3)cc12]

Step 1: Synthesis of 4-bromo-2-(hydroxyimino)-2,3-dihydro-1H-inden-1-one (Compound 1a)

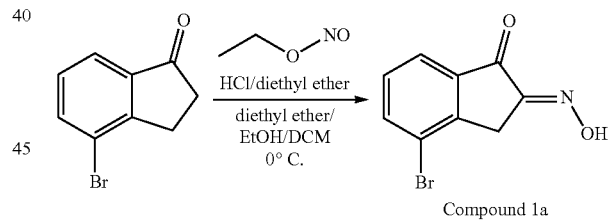

Compound 1a

4-Bromo-2,3-dihydro-1H-inden-1-one (10 g, 47.4 mmol, Ark Pharm, Inc.—AK-31085) was dissolved in mixture of diethyl ether (120 mL), ethanol (50 mL) and dichloromethane (20 mL). The reaction mixture was cooled down to 0° C. and 1M HCl in diethyl ether was added (24 mL, 24 mmol) followed by slow addition of 15% ethyl nitrite solution in ethanol (60 mL, 104 mmol) into the reaction mixture at 0° C. over 1 hour. The reaction mixture was vigorously stirred at room temperature for 3 hours and then concentrated down under reduced pressure. Diethyl ether was added (50 mL) and mixture was cooled down 0° C. Solid product was filtered off and washed twice with diethyl ether (2×20 mL) to yield the compound 1a. $^1$H NMR (400 MHz, DMSO-d$_6$) δ 12.83 (s, 1H), 7.98 (d, J=7.8 Hz, 1H), 7.77 (d, J=7.6 Hz, 1H), 7.62-7.22 (m, 1H), 3.67 (s, 2H). LCMS (m/z) 238.0 [M−H], Tr=2.10 min (LCMS method 1).

Step 2: Synthesis of 5-bromo-1,3-dichloroisoquinoline (Compound 1b)

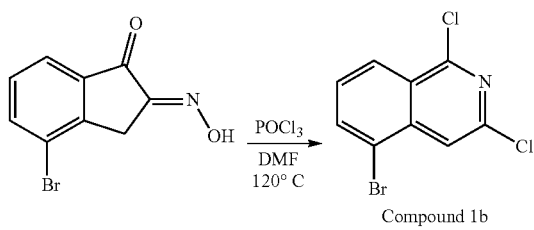
Compound 1b

Compound 1a (4.8 g, 20 mmol) was dissolved in phosphoryl chloride (60 mL). N,N-Dimethylformamide (0.5 mL) was added and the reaction mixture was heated in a sealed vessel at 120° C. for 30 minutes. The reaction mixture was cooled down and poured into crushed ice and vigorously stirred for 10 minutes. This mixture was treated in a sonic bath for 5 minutes. The solid compound was filtered off and washed with water (1 L) and then five times (5×50 mL) with a mixture of water/acetone/methanol (1/1/1) to afford the title compound 1b. $^1$H NMR (400 MHz, CDCl$_3$) δ 8.30 (d, J=8.5 Hz, 1H), 8.06-7.99 (m, 2H), 7.56-7.48 (m, 1H). LCMS (m/z) no MS signal, Tr=2.95 min (LCMS method 1).

Step 3: Synthesis of 5-bromo-3-chloroisoquinolin-1-amine (Compound 1c)

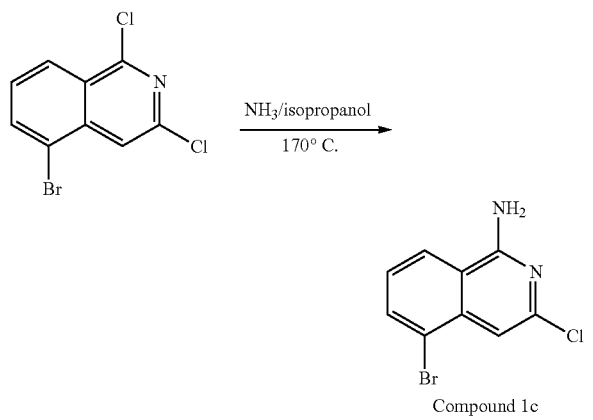
Compound 1c

Compound 1b (554 mg, 2.0 mmol) was taken up in a 2M ammonia solution in isopropanol (4 mL, 8 mmol) in a sealed microwave vessel. The reaction was heated at 170° C. by microwave for 2 hours. The reaction mixture was cooled down and diluted with water and dichloromethane. The organic layer was separated and washed twice with brine, dried over magnesium sulfate, filtered through a 2 cm layer of silica gel (which was washed with 5% methanol in dichloromethane). Combined organics were concentrated down under reduced pressure and the crude residue was treated with hexane in sonic bath for 2 minutes. Solid product was filtered off to afford title compound 1c. $^1$H NMR (400 MHz, DMSO-d$_6$) δ 8.24 (d, J=8.4 Hz, 1H), 8.00 (d, J=7.5 Hz, 1H), 7.60 (bs, 2H), 7.43-7.34 (m, 1H), 7.00 (s, 1H). LCMS (m/z) 257.2 [M+H], Tr=2.48 min (LCMS method 1).

Step 4: Synthesis of (E)-3-(4-bromo-3,5-dimethylphenyl)acrylonitrile (Compound 1d)

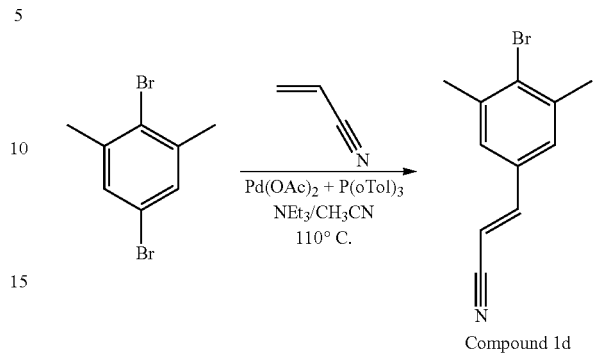
Compound 1d

To a solution of 2,5-dibromo-1,3-dimethylbenzene (2640 mg, 10 mmol, Oakwood Products, Inc.—018507) in anhydrous acetonitrile (25 mL) was added palladium(II) acetate (112 mg, 0.5 mmol), acrylonitrile (531 mg, 10 mmol), tri(o-tolyl)phosphine (131 mg, 0.5 mmol) and triethylamine (4 mL, 30 mmol) then the mixture was purged with argon and heated at 110° C. for 2 hours. The reaction mixture was filtered through Celite and the filter pad was washed with tetrahydrofuran (10 mL). The filtrate was evaporated then re-dissolved with ethyl acetate (50 mL). The solution was washed with water (50 mL). The water layer was back extracted with ethyl acetate (50 mL). The combined organics were washed with brine (30 mL), dried over sodium sulfate, filtered and concentrated under reduced pressure to give a crude residue. This was subjected to silica gel chromatography (gradient from 0-20% ethyl acetate in iso-hexanes) to afford the crude product which was treated in sonic bath with hexane (10 mL) for 10 minutes. The product precipitated out of solution and was collected by filtration. The solids were washed with cold hexane to afford compound 1d. $^1$H NMR (400 MHz, CDCl$_3$) δ 7.25 (d, J=16.6 Hz, 1H), 7.12 (s, 2H), 5.84 (d, J=16.6 Hz, 1H), 2.42 (s, 6H). LCMS (m/z) no MS signal, Tr=2.78 min (LCMS method 1).

Step 5: Synthesis of (E)-3-(3,5-dimethyl-4-(4,4,5,5-tetramethyl-1,3,2-dioxaborolan-2-yl)phenyl)acrylonitrile (Compound 1e)

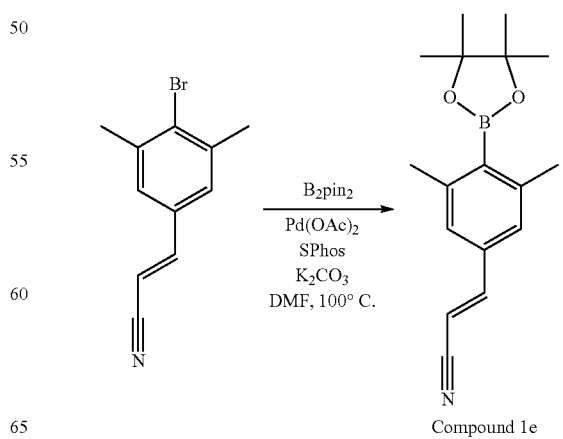
Compound 1e

A mixture of compound 1d (391 mg, 1.66 mmol), 4,4,4',4',5,5,5',5'-octamethyl-2,2'-Bi-(1,3,2-dioxaborolane) (630 mg, 2.48 mmol), potassium carbonate (687 mg, 5 mmol), palladium(II) acetate (19 mg, 0.08 mmol) and dicyclohexyl (2',6'-dimethoxy-[1,1'-biphenyl]-2-yl)phosphine (SPhos, 85 mg, 0.21 mmol) in dry DMF (20 mL) was purged with argon and heated at 100° C. for 1 hour. The reaction mixture was filtered through Celite and the filter pad was washed with tetrahydrofuran (10 mL). The filtrate was evaporated then re-dissolved with ethyl acetate (50 mL). The solution was washed with water (50 mL). The water layer was back extracted with ethyl acetate (50 mL). The combined organics were washed with brine (30 mL), dried over sodium sulfate, filtered and concentrated under reduced pressure to give a crude residue which was purified by silica gel chromatography (gradient from 0-20% ethyl acetate in iso-hexanes) to afford compound 1g. $^1$H NMR (400 MHz, CDCl$_3$) δ 7.28 (d, J=16.6 Hz, 1H), 7.00 (s, 2H), 5.84 (d, J=16.6 Hz, 1H), 2.39 (s, 6H), 1.37 (s, 12H). LCMS (m/z) 284.3 [M+H], Tr=2.85 min (LCMS method 1).

Step 6: synthesis of (E)-3-(4-(1-amino-3-chloroisoquinolin-5-yl)-3,5-dimethylphenyl)acrylonitrile (Compound 1f)

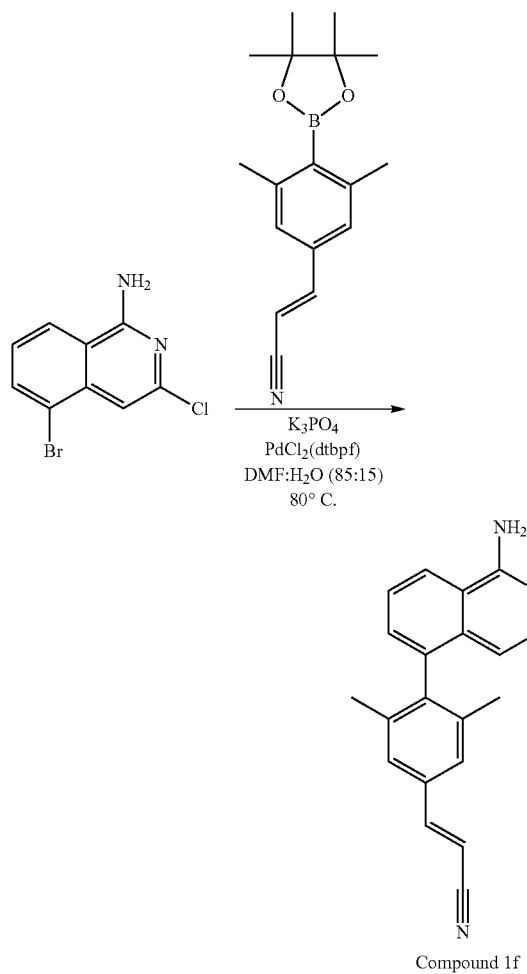

Compound 1f

Compound 1c (200 mg, 0.78 mmol), compound 1e (286 mg, 1.01 mmol), potassium phosphate tribasic (247 mg, 1.17 mmol) and 1,1'-bis(di-tert-butylphosphino)ferrocene palladium dichloride (51 mg, 0.08 mmol) were dissolved in N,N-dimethylformamide:water mixture (85:15, 40 mL) under argon. The reaction was heated to 80° C. for 30 minutes. The reaction mixture was cooled down to room temperature and diluted with water and ethyl acetate. The organic layer was separated and washed twice with brine, dried over magnesium sulfate, 0.5 volume equivalent of hexane added and this mixture was filtered through a 2 cm layer of silica gel which was washed with additional ethyl acetate. Combined organics were concentrated down under reduced pressure and the residue was treated with diethyl ether in a sonic bath. The solid product was filtered off and washed twice with diethyl ether and once with hexane to afford the title compound 1f. $^1$H NMR (400 MHz, DMSO-d$_6$) δ 8.26 (d, J=8.4 Hz, 1H), 7.65 (d, J=16.7 Hz, 1H), 7.59-7.53 (m, 1H), 7.51 (s, 2H), 7.48 (bs, 2H), 7.41 (d, J=7.1 Hz, 1H), 6.50 (d, J=16.7 Hz, 1H), 6.01 (s, 1H), 1.85 (s, 6H). LCMS (m/z) 334.2 [M+H], Tr=2.64 min (LCMS method 1).

Step 7: Synthesis of (E)-2-((1-amino-5-(4-(2-cyanovinyl)-2,6-dimethylphenyl)isoquinolin-3-yl)amino)pyrimidine-5-carbonitrile (Compound 1)

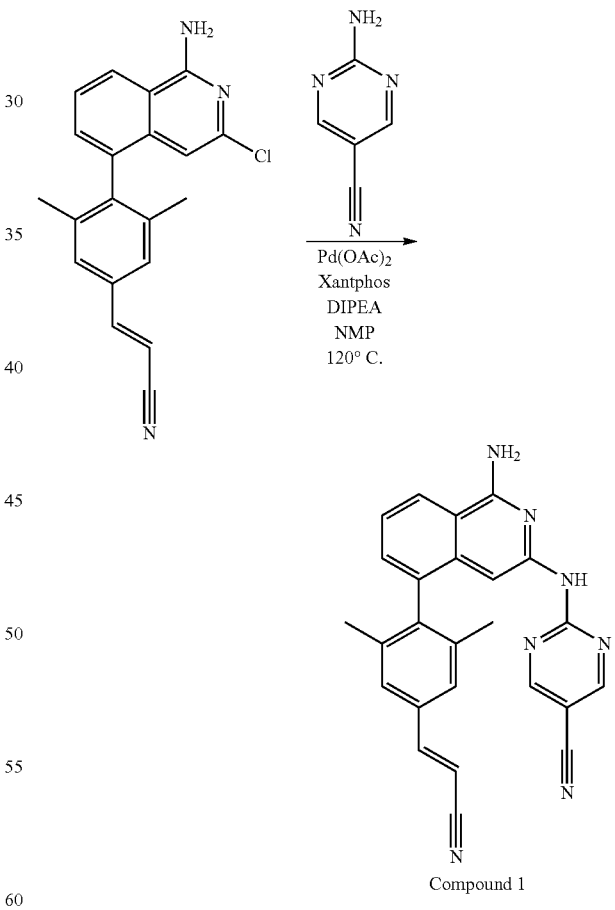

Compound 1

Compound 1f (200 mg, 0.60 mmol), 2-aminopyrimidine-5-carbonitrile (720 mg, 6.0 mmol, Ark Pharm Inc, AK-17302), N,N-diisopropylethylamine (835 μL, 4.78 mmol), (9,9-dimethyl-9H-xanthene-4,5-diyl)bis(diphenylphosphine) (35 mg, 0.06 mmol) and palladium (II) acetate (13 mg, 0.06 mmol) were combined under argon in N-methyl-2-pyrrolidone (1 mL). The reaction was heated at 120° C. in a sealed vessel for 4 hours. The reaction mixture was cooled to room temperature and purified by reverse phase chromatography (20-60% acetonitrile in water with 0.1% trifluoroacetic acid) to afford the TFA salt of compound 1. ¹H NMR (400 MHz, methanol-d₄) δ 8.87 (s, 2H), 8.40 (dt, J=8.1, 1.2 Hz, 1H), 7.76-7.49 (m, 3H), 7.48 (s, 2H), 6.29 (d, 0.1=16.6 Hz, 1H), 6.27 (s, 1H), 1.97 (s, 6H). LCMS (m/z) 418.3 [M+H], Tr=1.40 min (LCMS method 2).

EXAMPLE 2

(E)-5-((1-Amino-5-(4-(2-cyanovinyl)-2,6-dimethylphenyl)isoquinolin-3-yl)amino)pyrazine-2-carbonitrile—Compound 2

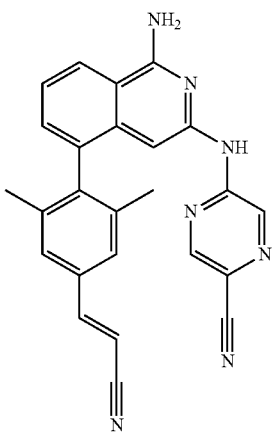

Synthesis of (E)-5-((1-amino-5-(4-(2-cyanovinyl)-2,6-dimethylphenyl)isoquinolin-3-yl)amino)pyrazine-2-carbonitrile (Compound 2)

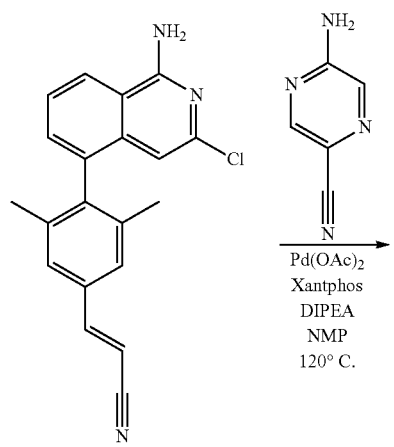

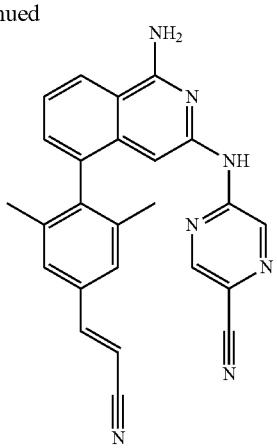

Compound 2

Compound 1f (200 mg, 0.60 mmol), 5-aminopyrazine-2-carbonitrile (163 mg, 1.36 mmol, Ark Pharm Inc, AK-21935), N,N-diisopropylethylamine (835 μL, 4.78 mmol), (9,9-dimethyl-9H-xanthene-4,5-diyl)bis(diphenylphosphine) (35 mg, 0.06 mmol) and palladium (II) acetate (13 mg, 0.06 mmol) were combined under argon in N-methyl-2-pyrrolidone (1 mL). The reaction was heated at 120° C. in a sealed vessel for 4 hours. The reaction mixture was cooled to room temperature and purified by reverse phase chromatography (20-60% acetonitrile in water with 0.1% trifluoroacetic acid) to afford the TFA salt of compound 2. ¹H NMR (400 MHz, Methanol-d₄) δ 8.55 (d, J=1.4 Hz, 1H), 8.36 (dd, J=8.1, 1.4 Hz, 1H), 8.31 (d, J=1.4 Hz, 1H), 7.73-7.54 (m, 3H), 7.48 (s, 2H), 6.30 (d, J=16.7 Hz, 1H), 6.16 (s, 1H), 1.97 (s, 6H). LCMS (m/z) 418.3 [M+H], Tr=1.57 min (LCMS method 3).

EXAMPLE 3

(E)-6-((1-Amino-5-(4-(2-cyanovinyl)-2,6-dimethylphenyl)isoquinolin-3-yl)amino)pyridazine-3-carbonitrile—Compound 3

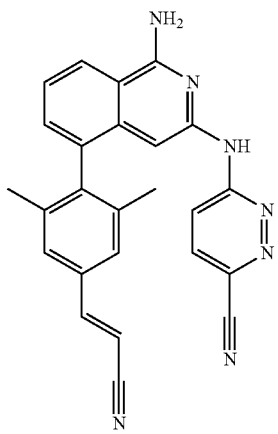 [SMILES: Cc1cc(/C=C/C#N)cc(C)c1-c1cccc2c(N)nc(Nc3ccc(C#N)nn3)cc12]

Synthesis of (E)-6-((1-amino-5-(4-(2-cyanovinyl)-2,6-dimethylphenyl)isoquinolin-3-yl)amino)pyridazine-3-carbonitrile (Compound 3)

EXAMPLE 4

(E)-6-((1-Amino-5-(4-(2-cyanovinyl)-2,6-dimethylphenyl)isoquinolin-3-yl)amino)nicotinonitrile—Compound 4

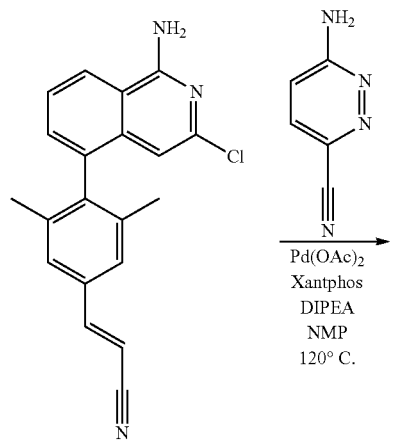

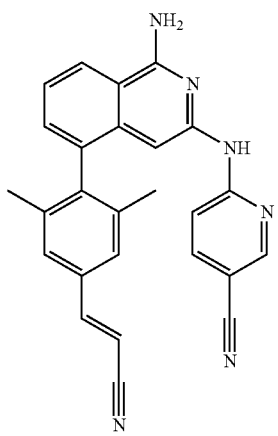 [SMILES: Cc1cc(/C=C/C#N)cc(C)c1-c1cccc2c(N)nc(Nc3ccc(C#N)cn3)cc12]

Synthesis of (E)-6-((1-amino-5-(4-(2-cyanovinyl)-2,6-dimethylphenyl)isoquinolin-3-yl)amino)nicotinonitrile (Compound 4)

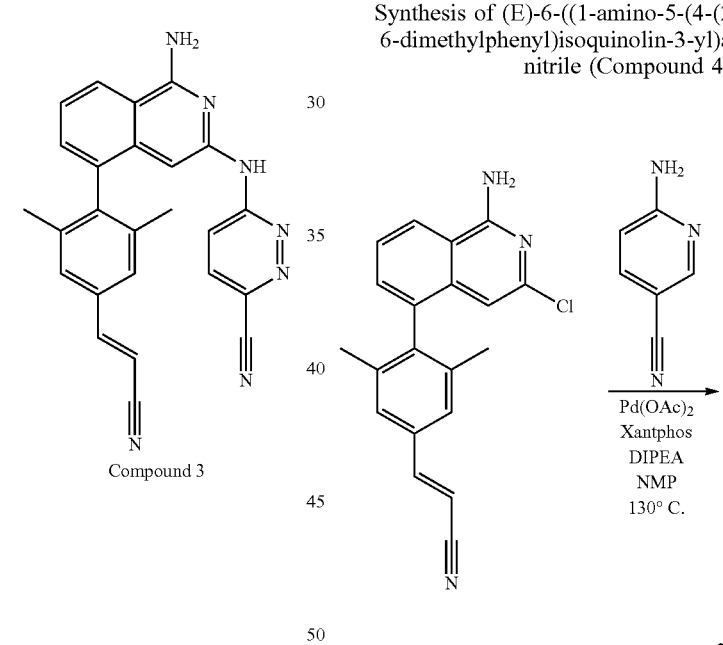

Compound 3

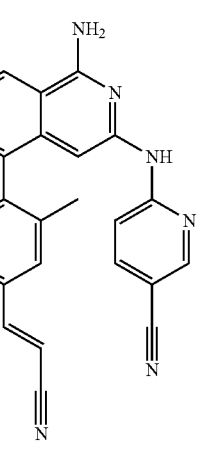

Compound 4

Compound if (200 mg, 0.60 mmol), 6-aminopyridazine-3-carbonitrile (163 mg, 1.36 mmol, Matrix Scientific, 112287), N,N-diisopropylethylamine (835 µL, 4.78 mmol), (9,9-dimethyl-9H-xanthene-4,5-diyl)bis(diphenylphosphine) (35 mg, 0.06 mmol) and palladium (II) acetate (13 mg, 0.06 mmol) were combined under argon in N-methyl-2-pyrrolidone (1 mL). The reaction was heated at 120° C. in a sealed vessel for 4 hours. The reaction mixture was cooled to room temperature and purified by reverse phase chromatography (20-60% acetonitrile in water with 0.1% trifluoroacetic acid) to afford the TFA salt of compound 3. $^1$H NMR (400 MHz, Methanol-$d_4$) δ 8.45-8.31 (m, 1H), 7.94 (d, J=9.3 Hz, 1H), 7.81-7.43 (m, 5H), 7.24 (d, J=9.3 Hz, 1H), 6.30 (d, J=16.7 Hz, 1H), 6.10 (s, 1H), 1.97 (s, 6H). LCMS (m/z) 418.3 [M+H], Tr=1.41 min (LCMS method 2).

Compound 1f (200 mg, 0.60 mmol), 6-aminonicotinonitrile (214 mg, 1.80 mmol, Ark Pharm Inc, AK-32349), N,N-diisopropylethylamine (835 µl, 4.78 mmol), (9,9-dimethyl-9H-xanthene-4,5-diyl)bis(diphenylphosphine) (35 mg, 0.06 mmol) and palladium (II) acetate (13 mg, 0.06 mmol) were combined under argon in N-methyl-2-pyrrolidone (10 mL). The reaction was heated at 130° C. in a sealed vessel for 3 days. The reaction mixture was cooled down to room temperature and diluted with water and ethyl acetate. The organic layer was separated and washed twice with brine, dried over magnesium sulfate, 0.05 volume equivalent of hexane added and this mixture was filtered through a 2 cm layer of silica gel which was washed with additional ethyl acetate. Combined organics were concentrated down under reduced pressure. The crude residue was purified by reverse phase chromatography (10-80% acetonitrile in water with 0.1% trifluoroacetic acid) to afford the TFA salt of compound 4. $^1$H NMR (400 MHz, DMSO-$d_6$) δ 8.53 (s, 1H), 8.39-8.29 (m, 1H), 8.11-7.97 (m, 1H), 7.68 (d, J=16.7 Hz, 1H), 7.62-7.32 (m, 5H), 6.52 (d, J=16.7 Hz, 1H), 6.09 (s, 1H), 1.90 (s, 6H). LCMS (m/z) 417.3 [M+H], Tr=2.21 min (LCMS method 1).

EXAMPLE 5

(E)-6-((5-(4-(2-Cyanovinyl)-2,6-dimethylphenyl)isoquinolin-3-yl)amino)nicotinonitrile—Compound 5

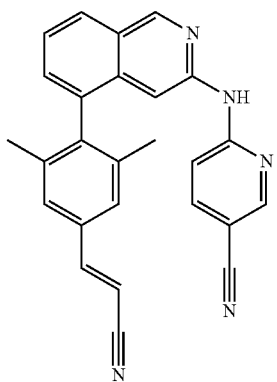

Compound 5

Step 1: Synthesis of (E)-3-(4-(3-chloroisoquinolin-5-yl)-3,5-dimethylphenyl)acrylonitrile (Compound 5a)

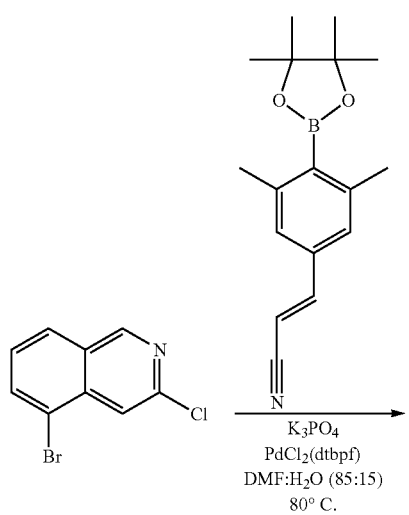

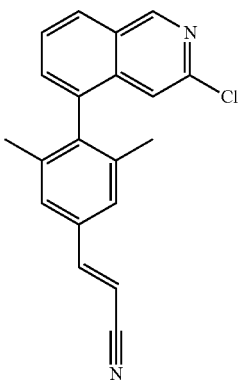

Compound 5a

5-Bromo-3-chloroisoquinoline (500 mg, 2.06 mmol; SynQuest Laboratories; #3H32-D-Z7), compound 1e (759 mg, 2.68 mmol), potassium phosphate tribasic (656 mg, 3.09 mmol) and 1,1'-bis(di-tert-butylphosphino)ferrocene palladium dichloride (134 mg, 0.21 mmol) were dissolved in dimethylformamide:water mixture (85:15, 40 mL) under argon. The reaction was heated to 80° C. for 30 minutes. The reaction mixture was cooled down to room temperature and diluted with water and ethyl acetate. The organic layer was separated and washed twice with brine, dried over magnesium sulfate, 0.5 volume equivalent of hexane added and this mixture was filtered through a 2 cm layer of silica gel which was washed with additional ethyl acetate. Combined organics were concentrated down under reduced pressure and the residue was treated with hexane in a sonic bath. The solid product was filtered off and washed twice with hexane to afford the title compound 5a. $^1$H NMR (400 MHz, DMSO-d6) δ 9.34 (s, 1H), 8.31-8.17 (m, 1H), 7.84 (dd, J=8.2, 7.1 Hz, 1H), 7.74-7.60 (m, 2H), 7.56 (s, 2H), 7.00 (s, 1H), 6.53 (d, J=16.7 Hz, 1H), 1.84 (s, 6H). LCMS (m/z) 319.2 [M+H], Tr=2.83 min (LCMS method 1).

Step 2: Synthesis of (E)-6-((5-(4-(2-cyanovinyl)-2,6-dimethylphenyl)isoquinolin-3-yl)amino)nicotinonitrile (Compound 5)

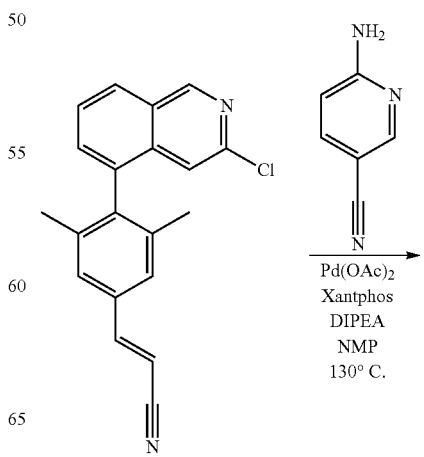

-continued

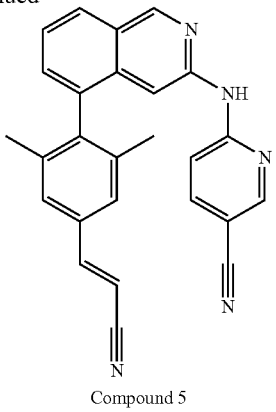

Compound 5

Compound 5a (400 mg, 1.26 mmol), 6-aminonicotinonitrile (448 mg, 3.76 mmol, Ark Pharm Inc, AK-32349), N,N-diisopropylethylamine (1.73 mL, 10 mmol), (9,9-dimethyl-9H-xanthene-4,5-diyl)bis(diphenylphosphine) (73 mg, 0.13 mmol) and palladium (II) acetate (28 mg, 0.13 mmol) were combined under argon in N-methyl-2-pyrrolidone (40 mL). The reaction was heated at 120° C. in a sealed vessel for 12 hours. The reaction mixture was cooled down to room temperature and diluted with water and ethyl acetate. The organic layer was separated and washed twice with brine, dried over magnesium sulfate, 0.05 volume equivalent of hexane added and this mixture was filtered through a 2 cm layer of silica gel which was washed with additional ethyl acetate. Combined organics were concentrated down under reduced pressure. The crude residue was purified by reverse phase chromatography (10-80% acetonitrile in water with 0.1% trifluoroacetic acid) to afford the TFA salt of compound 5. $^1$H NMR (400 MHz, DMSO-d$_6$) δ 10.41 (bs, 1H), 9.24 (d, J=0.9 Hz, 1H), 8.35 (dd, J=2.3, 0.8 Hz, 1H), 8.10 (dt, J=8.3, 1.1 Hz, 1H), 7.98 (dd, J=8.9, 2.3 Hz, 1H), 7.70 (d, J=16.7 Hz, 1H), 7.63-7.55 (m, 5H), 7.50 (dd, J=7.0, 1.2 Hz, 1H), 6.54 (d, J=16.7 Hz, 1H), 1.90 (s, 6H). LCMS (m/z) 402.3 [M+H], Tr=2.86 min (LCMS method 1).

EXAMPLE 6

(E)-4-((5-(4-(2-Cyanovinyl)-2,6-dimethylphenyl) isoquinolin-3-yl)amino)benzonitrile—Compound 6

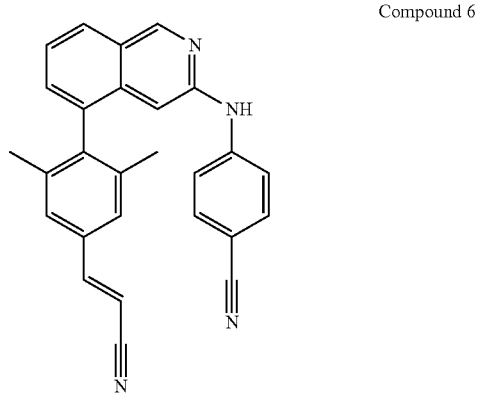 [SMILES: Cc1cc(/C=C/C#N)cc(C)c1-c1cccc2cnc(Nc3ccc(C#N)cc3)cc12]

Compound 6

Synthesis of (E)-4-((5-(4-(2-cyanovinyl)-2,6-dimethylphenyl)isoquinolin-3-yl)amino)benzonitrile (Compound 6)

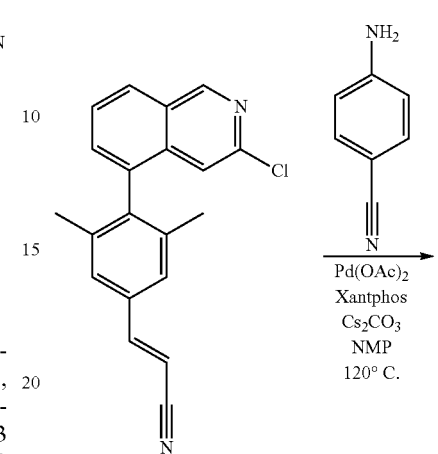

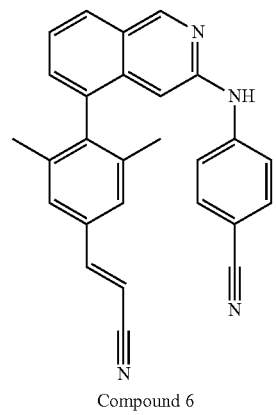

Compound 6

Compound 5a (20 mg, 0.063 mmol), 4-aminobenzonitrile (10 mg, 0.082 mmol, Sigma-Aldrich), cesium carbonate (31 mg, 0.094 mmol), (9,9-dimethyl-9H-xanthene-4,5-diyl)bis (diphenylphosphine) (2 mg, 0.003 mmol) and palladium (II) acetate (1 mg, 0.003 mmol) were combined under argon in N-methyl-2-pyrrolidone (1 mL). The reaction was heated at 120° C. in a sealed vessel for 5 hours. The reaction mixture was cooled to room temperature and purified by reverse phase chromatography (20-100% acetonitrile in water with 0.1% trifluoroacetic acid) to afford the TFA salt of compound 6. $^1$H NMR (400 MHz, DMSO-d$_6$) δ 9.64 (s, 1H), 9.21 (d, J=0.8 Hz, 1H), 8.06 (d, J=8.3 Hz, 1H), 7.80-7.73 (m, 2H), 7.72-7.58 (m, 4H), 7.56 (s, 2H), 7.51 (dd, J=8.3, 6.9 Hz, 1H), 7.41 (dd, J=6.9, 1.2 Hz, 1H), 6.53 (d, J=16.7 Hz, 1H), 1.89 (s, 6H). LCMS (m/z) 401.3 [M+H], Tr=3.15 min (LCMS method 1).

BIOLOGICAL EXAMPLES

Example A

High Throughput Screening of Anti-HIV-1 RT (Reverse Transcriptase)

Compounds were screened in a miniaturized, high throughput cytopathic effect assay for activity against HIV-1 HBX2 (wild type) and HIV-1 reverse transcriptase mutants K103N and Y181C. In Tables 1 and 2 below, "w.t." refers to results of the tested compounds run with the wildtype 1 and "w.t. assay 2" refers results of the tested compounds run with the wildtype on the same day as the testing of the compounds with the mutants. Thus, "w.t. assay 2" was run under the same conditions as the testing of the compounds with the mutants and provides a direct comparison with the results from the testing with the mutants.

Ten-point serial dilutions of compounds with half-log step size were generated in DMSO. AZT (5 µM) was used as the positive control and DMSO as the negative control. The Echo acoustic dispenser was used to deliver 200 nL of serially diluted compound into sterile 384 well tissue culture assay plates. Two million MT-4 cells were incubated with each of the 3 viruses at MOI of 0.0005 in separate 1 mL infection tubes for 1 hour at 37° C. The cells were diluted in cell culture medium (RPMI+10% FBS) to 50,000 cells/mL. The infected cells were added to 384 well assay plates containing serially dilute compounds. Assay plates were incubated for 5 days in a humidified incubator set at 37° C. and 5% $CO_2$. To measure the cytopathic effect of HIV, 40 µL Cell TiterGlo was added to each well and the resulting luminescence signal is read with the Envision plate reader (Perkin Elmer). Data were normalized to positive and negative controls in each plate and expressed as % CPE Protection. $EC_{50}$ values were defined as the compound concentration that caused a 50% decrease in luminescence signal, and were calculated by non-linear regression using Pipeline Pilot software by applying a four parameter fit equation (Accelrys, San Diego, Calif.). Results are disclosed in Table 1.

TABLE 1

| Compound ID | MT4 $EC_{50}$ (nM) against w.t. | MT4 $EC_{50}$ (nM) against | | FC against mutant | |
|---|---|---|---|---|---|
| | w.t. | assay 2 | K103N | Y181C | K103N | Y181C |
| 1 | 6.4 | 4.5 | 6.4 | 51.6 | 1.4 | 11.5 |
| 2 | 14.4 | 20.2 | 29.7 | 109.2 | 1.5 | 5.4 |
| 3 | 17.0 | 22.7 | 36.4 | 174.0 | 1.6 | 7.7 |
| 4 | 2.8 | 3.6 | 3.7 | 12.0 | 1.0 | 3.4 |
| 5 | 4.2 | 4.7 | 4.7 | 12.0 | 1.0 | 2.5 |
| 6 | 12.9 | NA | NA | NA | NA | NA |

The high-throughput screening was also run for nevirapine ("NPV"), rilpivirine ("RPV"), and efavirenz ("EFV"). Nevirapine was obtained from Toronto Research Chemicals, Inc. (Toronto, Canada; Catalogue #N391275). Rilpivirine was obtained from Key Organics Ltd. (Camelford, Cornwall, United Kingdom; Catalogue #KE-0036). Efavirenz was obtained from Toronto Research Chemicals, Inc. (Toronto, Canada; Catalogue #E425000). The results are shown below in Table 2. Further details and background can be found in Janssen et al, J. Med. Chem, 2005, 48, 1901-1909; Das et al., Proc. Nat. Acad. Sci., 2008, vol., 105, no. 5, 1466-1471; and Kuroda et al., Nature Chemistry, 2013, DOI: 10.1038/NCHEM.1559.

TABLE 2

| Compound | MT4 $EC_{50}$ (nM) against w.t. | MT4 $EC_{50}$ (nM) against | | FC against mutant | |
|---|---|---|---|---|---|
| | w.t. | assay 2* | K103N | Y181C | K103N | Y181C |
| Nevirapine ("NVP") | 65.0 | ND | ND | ND | ND | ND |
| Rilpivirine ("RPV") | 0.9 | 1.3 | 1.5 | 3.8 | 1.2 | 3.1 |
| Efavirenz ("EFV") | 1.3 | 1.6 | 46.4 | 3.8 | 28.9 | 2.3 |

*w.t. assay 2 were run on the same day as the assays with K103N and Y181C mutants.
ND: not determined It is understood that $EC_{50}$ may be evaluated by techniques known in the art. In one embodiment, the compounds exhibit an $EC_{50}$ of less than about 3000 nM in the wild-type or any of the HIV RT mutants (e.g., K103N and Y181C), as measured by the method provided in the "high throughput screening of anti-HIV mutants K103N and Y181C" assay section discussed above. In one embodiment, the compounds exhibit an $EC_{50}$ of less than about 1000 nM, 500 nM, 400 nM, 300 nM, 250 nM, 200 nM, 100 nM, 50 nM, 25 nM, 10 nM, 5 nM, or 1 nM in the wild-type or any of the HIV RT mutants (e.g., K103N and Y181C).

Example B hERG Assay

Cells:
AVIVA's CHO cell line, which stably expresses hERG channels, was used for the study. Cells were cultured in DMEM/F12 containing 10% FBS, 1% penicillin/streptomycin and 500 µg/ml G418. Before testing, cells were harvested using Accumax (Innovative Cell Technologies).

Solutions:
For electrophysiological recordings, the following solutions were used:
External Solution: 2 mM $CaCl_2$; 2 mM $MgCl_2$; 4 mM KCl; 150 mM NaCl; 10 mM Glucose; 10 mM HEPES; 305-315 mOsm; pH 7.4 (adjusted with 5M NaOH.)
Internal Solution: 140 mM KCl; 10 mM $MgCl_2$; 6 mM EGTA; 5 mM HEPES-Na; 5 mM ATP-Mg; 295-305 mOsm; pH 7.25 (adjusted with 1M KOH).

Electrophysiology:
Whole cell recordings were performed using PX 7000A (Axon Instruments) with AVIVA's SealChip™ technology. Cells were voltage clamped at a holding potential of −80 mV. The hERG current was then activated by a depolarizing step to −50 mV for 300 ms. This first step at −50 mV was used as a baseline for measuring peak amplitude of the tail current. Next, a voltage step to +20 mV was applied for 5 s to activate the channels. Finally, a step back to −50 mV for 5 s removed activation and the deactivating tail current was recorded.

Test Article Handling and Dilutions:
All test articles were prepared from 10 mM DMSO stock solutions. Solutions were mixed by sonication for 20 min, followed by vigorous vortexing. Prior to testing, compounds were diluted to test concentrations in glass vials using External Solution. Dilutions were prepared no longer than 20 min prior to use.

Electrophysiology Procedures

After achieving whole cell configuration, cells were monitored for 90 s to assess stability and then washed with External Solution for 66 s. The voltage protocol was then applied to the cells every 12 s throughout the procedure. Only stable cells with recording parameters above threshold were allowed to enter the drug addition procedure.

External solution containing 0.1% DMSO (vehicle) was applied to the cells to establish a baseline. After allowing the current to stabilize for 3 to 10 min, test articles were applied. Test article solutions were added to cells in 4 separate additions. Cells were kept in test solution until effect of the test article reached steady state, to a maximum of 12 min. Next, 1 µM cisapride (positive control) was added. Finally, washout with External Solution was performed until the recovery current reached steady state.

Data Analysis

Data analysis was performed using DataXpress (Axon Instruments), Clampfit (Axon Instruments) and Origin (OriginLab Corporation) software. Results are disclosed in Table 3.

TABLE 3

| Compound No. | hERG |
| --- | --- |
| 1 | NA |
| 2 | NA |
| 3 | NA |
| 4 | 3 µM |
| 5 | NA |
| 6 | NA |

The hERG assay was also run for rilpivirine ("RPV"). The result was 0.5 µM.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present disclosure.

The Examples disclosed herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

All references, including publications, patents, and patent documents are incorporated by reference herein, as though individually incorporated by reference. The present disclosure provides reference to various embodiments and techniques. However, it should be understood that many variations and modifications may be made while remaining within the spirit and scope of the present disclosure.

What is claimed is:

1. A compound of Formula I:

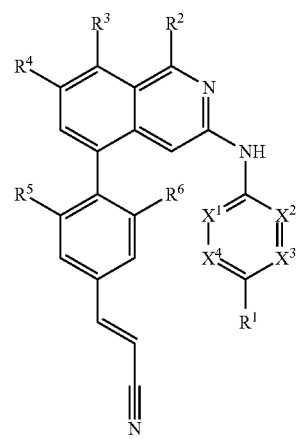

or a tautomer or pharmaceutically acceptable salt thereof, wherein $X^1$, $X^2$, $X^3$, and $X^4$ are each independently $C(R^7)$ or N, wherein 0 to 2 of $X^1$, $X^2$, $X^3$, and $X^4$ are N;

$R^1$ is —H, —CN, —OR$^a$, $C_{1-6}$ haloalkyl or halogen;

$R^2$ is —H, —NR$^b$R$^c$, —SR$^a$, —OR$^a$ or $C_{1-6}$ alkyl, wherein $C_{1-6}$ alkyl is optionally substituted with 1, 2, 3, 4 or 5 $R^8$ groups, which may be the same or different;

$R^3$ and $R^4$ are each independently —H, —OR$^a$, halogen, —NR$^b$R$^c$, —C(O)OR$^a$, —CN, —C(O)NR$^b$R$^c$, —NHC(O)NR$^b$R$^c$, —OC(O)NR$^b$R$^c$, CH$_2$C(O)NR$^b$R$^c$, $C_{1-6}$ alkyl or $C_{1-6}$ heteroalkyl, wherein each $C_{1-6}$ alkyl or $C_{1-6}$ heteroalkyl is optionally substituted with 1, 2, 3, 4 or 5 $R^8$ groups, which may be the same or different;

$R^5$ and $R^6$ are each independently halogen, —OR$^a$ or $C_{1-6}$ alkyl, wherein each $C_{1-6}$ alkyl is optionally substituted with 1, 2, 3, 4 or 5 $R^8$ groups, which may be the same or different;

each $R^7$ is independently —H, halogen, —OR$^a$ or $C_{1-6}$ alkyl, wherein each $C_{1-6}$ alkyl is optionally substituted with 1, 2, 3, 4 or 5 $R^8$ groups, which may be the same or different;

each $R^8$ is independently $C_{1-6}$ alkyl, $C_{1-6}$ heteroalkyl, aryl, heteroaryl, halogen, —OR$^a$, —C(O)R$^a$, —C(O)OR$^a$, —C(O)NR$^b$R$^c$, —OC(O)NR$^b$R$^c$, —NR$^b$C(O)OR$^a$, —SR$^a$, —S(O)$_{1-2}$R$^a$, —S(O)$_2$F, —S(O)$_2$NR$^b$R$^c$, —NR$^b$S(O)$_2$R$^a$, —N$_3$, —CN or —NO$_2$, wherein each $C_{1-6}$ alkyl, $C_{1-6}$ heteroalkyl, aryl or heteroaryl is optionally substituted with 1, 2, 3, 4 or 5 halogen, —OR$^a$, —C(O)R$^a$, —C(O)OR$^a$, —C(O)NR$^b$R$^c$, —OC(O)NR$^b$R$^c$, —NR$^b$C(O)OR$^a$, —SR$^a$, —S(O)$_{1-2}$R$^a$, —S(O)$_2$F, —S(O)$_2$NR$^b$R$^c$, —NR$^b$S(O)$_2$R$^a$, —N$_3$, —CN or —NO$_2$ groups, which may be the same or different;

each $R^a$ is independently —H, $C_{1-6}$ alkyl, $C_{1-6}$ haloalkyl, $C_{1-6}$ heteroalkyl, aryl or heteroaryl, wherein each aryl or heteroaryl is optionally substituted with 1, 2, 3, 4 or 5 $R^{21}$ groups, which may be the same or different;

$R^b$ and $R^c$ are each independently —H, —NH$_2$, $C_{1-6}$ alkyl, $C_{1-6}$ heteroalkyl, aryl or heteroaryl, wherein each $C_{1-6}$ alkyl, $C_{1-6}$ heteroalkyl, aryl or heteroaryl is optionally substituted with 1, 2, 3, 4 or 5 $R^{21}$ groups; or $R^b$ and $R^c$ together with the atoms to which they are attached form a $C_{1-10}$ heterocycloalkyl;

$R^{21}$ is $C_{1-6}$ alkyl, —CN, aryl, heteroaryl or halogen.

2. The compound of claim 1, or a tautomer or a pharmaceutically acceptable salt thereof, wherein $R^2$ is —H, —$NR^bR^c$ or —OH.

3. The compound of claim 1, or a tautomer or a pharmaceutically acceptable salt thereof, wherein $R^2$ is —H, —$NH_2$ or —OH.

4. The compound of claim 1, or a tautomer or a pharmaceutically acceptable salt thereof, wherein $R^3$ and $R^4$ are each independently —H, —$OR^a$, halogen, —$NR^bR^c$, —$C(O)OR^a$, or —$C(O)NR^bR^c$.

5. The compound of claim 1, or a tautomer or a pharmaceutically acceptable salt thereof, wherein $R^3$ and $R^4$ are each —H.

6. The compound of claim 1, wherein the compound of Formula I is a compound of Formula Ia:

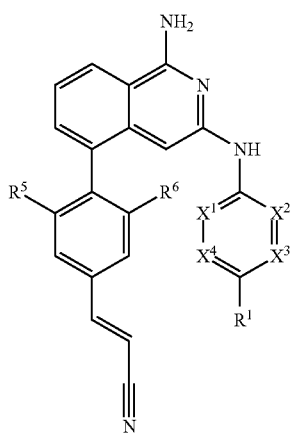

Ia or a tautomer or pharmaceutically acceptable salt thereof.

7. The compound of claim 1, or a tautomer or a pharmaceutically acceptable salt thereof, wherein

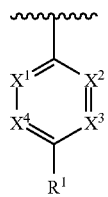

is selected from

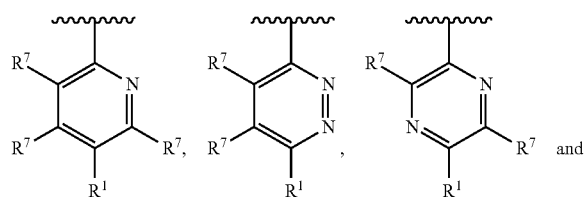

and

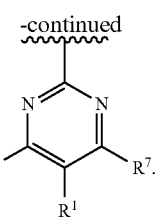

8. The compound of claim 1, wherein the compound of Formula I is a compound of Formula Ib:

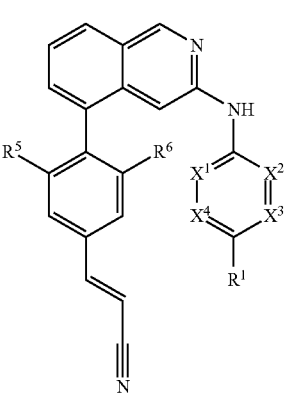

Ib or a tautomer or pharmaceutically acceptable salt thereof.

9. The compound of claim 8, or a tautomer or a pharmaceutically acceptable salt thereof, wherein

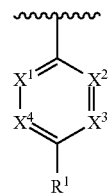

is

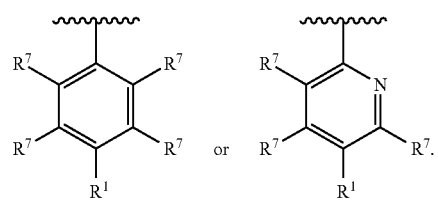

10. The compound of claim 1, or a tautomer or a pharmaceutically acceptable salt thereof, wherein $R^5$ and $R^6$ are each independently halogen, —O—$C_{1-6}$ alkyl or $C_{1-6}$ alkyl, wherein each $C_{1-6}$ alkyl is optionally substituted with 1, 2, 3, 4 or 5 $R^8$ groups, which may be the same or different.

11. The compound of claim 1, or a tautomer or a pharmaceutically acceptable salt thereof, wherein $R^1$ is —H, —CN, —O—$C_{1-6}$ alkyl, —$CF_3$, —O—$C_{1-3}$ haloalkyl or halogen.

12. The compound of claim 1, or a tautomer or a pharmaceutically acceptable salt thereof, wherein $R^1$=—CN.

13. The compound of claim 1, or a tautomer or a pharmaceutically acceptable salt thereof, wherein each $R^7$ is independently —H, halogen, —O—$C_{1-6}$ alkyl or $C_{1-6}$ alkyl, wherein each $C_{1-6}$ alkyl is optionally substituted with 1, 2, 3, 4 or 5 $R^8$ groups, which may be the same or different.

14. The compound of claim 1, or a tautomer or a pharmaceutically acceptable salt thereof, wherein each $R^7$ is —H.

15. The compound of claim 1, wherein the compound is selected from

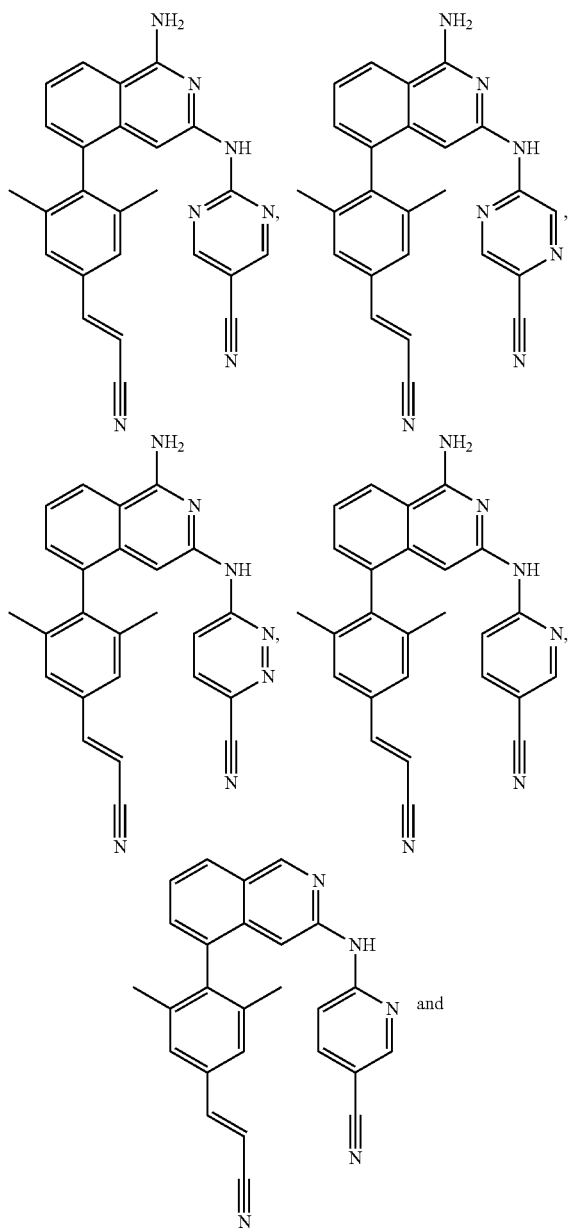

or a tautomer or pharmaceutically acceptable salt thereof.

16. A pharmaceutical composition comprising a compound of claim 1, or a tautomer or pharmaceutically acceptable salt thereof, and a pharmaceutically acceptable carrier.

17. The pharmaceutical composition of claim 16, further comprising at least one or more additional therapeutic agents.

18. The pharmaceutical composition of claim 17, wherein the at least one or more additional therapeutic agents is selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof.

19. A method of inhibiting reverse transcriptase in a subject in need thereof, comprising administering a compound of claim 1, or a tautomer or pharmaceutically acceptable salt thereof, to the subject.

20. A method for treating an HIV infection in a subject comprising administering to the subject a compound of claim 1, or a tautomer or pharmaceutically acceptable salt thereof.

21. A method for treating an HIV infection in a subject comprising administering to the subject in need thereof a compound of claim 1, or a tautomer or pharmaceutically acceptable salt thereof, in combination with a therapeutically effective amount of one, two, three, or four additional therapeutic agents independently selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof.

* * * * *